United States Patent [19]
Hosaka

[11] Patent Number: 5,895,348
[45] Date of Patent: Apr. 20, 1999

[54] DEVICE FOR ACTIVATING CELLS OF A HUMAN BODY

[75] Inventor: Einosuke Hosaka, Yokohama, Japan

[73] Assignee: Soko Co., Ltd., Tokyo, Japan

[21] Appl. No.: 08/656,915

[22] Filed: May 30, 1996

[30] Foreign Application Priority Data

| Jan. 30, 1996 | [JP] | Japan | 8-000235 U |
| Jan. 30, 1996 | [JP] | Japan | 8-014239 |
| Feb. 29, 1996 | [JP] | Japan | 8-043059 |

[51] Int. Cl.$^6$ ........................ A61H 1/00
[52] U.S. Cl. ........................ 600/27; 600/28
[58] Field of Search ........................ 601/1; 606/27; 600/26–28

[56] References Cited

U.S. PATENT DOCUMENTS

| 3,132,688 | 5/1964 | Nowak. | |
| 4,064,376 | 12/1977 | Yamada | 179/146 H |
| 4,315,502 | 2/1982 | Gorges | 600/27 |
| 4,753,225 | 6/1988 | Vogel. | |
| 4,967,871 | 11/1990 | Komatsubara | 181/141 |
| 5,035,235 | 7/1991 | Chesky | 128/33 |
| 5,086,755 | 2/1992 | Schmid-Eilber | 128/33 |
| 5,100,373 | 3/1992 | Liboff. | |
| 5,101,810 | 4/1992 | Skille et al. | 128/33 |
| 5,125,033 | 6/1992 | Lee | 381/199 |
| 5,266,070 | 11/1993 | Hagiwara et al. | 600/27 |
| 5,387,178 | 2/1995 | Moses | 600/27 |
| 5,553,148 | 9/1996 | Werle | 601/86 |

FOREIGN PATENT DOCUMENTS

| 4375185 | 1/1986 | Australia. |
| 1178888 | 2/1988 | Australia. |
| 3019189 | 8/1989 | Australia. |
| 3304889 | 10/1989 | Australia. |
| 7289191 | 9/1991 | Australia. |
| 4441093 | 2/1995 | Australia. |
| 0330472 | 8/1989 | European Pat. Off.. |
| 5269175 | 10/1993 | Japan. |
| 6269484 | 9/1994 | Japan. |
| 7327288 | 12/1995 | Japan. |
| WO 90/04379 | 5/1990 | WIPO. |
| WO 93/24093 | 12/1993 | WIPO. |
| WO 94/13357 | 6/1994 | WIPO. |
| WO 95/04508 | 2/1995 | WIPO. |
| WO 96/04879 | 2/1996 | WIPO. |
| WO 87/05497 | 9/1997 | WIPO. |

*Primary Examiner*—Francis J. Jaworski
*Attorney, Agent, or Firm*—Greer, Burns & Crain, Ltd.

[57] ABSTRACT

A device for activating cells over a prolonged period, comprises a stimuli imparting device for imparting stimuli to a human body, and a state changing device for changing the state of the stimuli imparted by the stimuli imparting device.

1 Claim, 26 Drawing Sheets

FIG.1
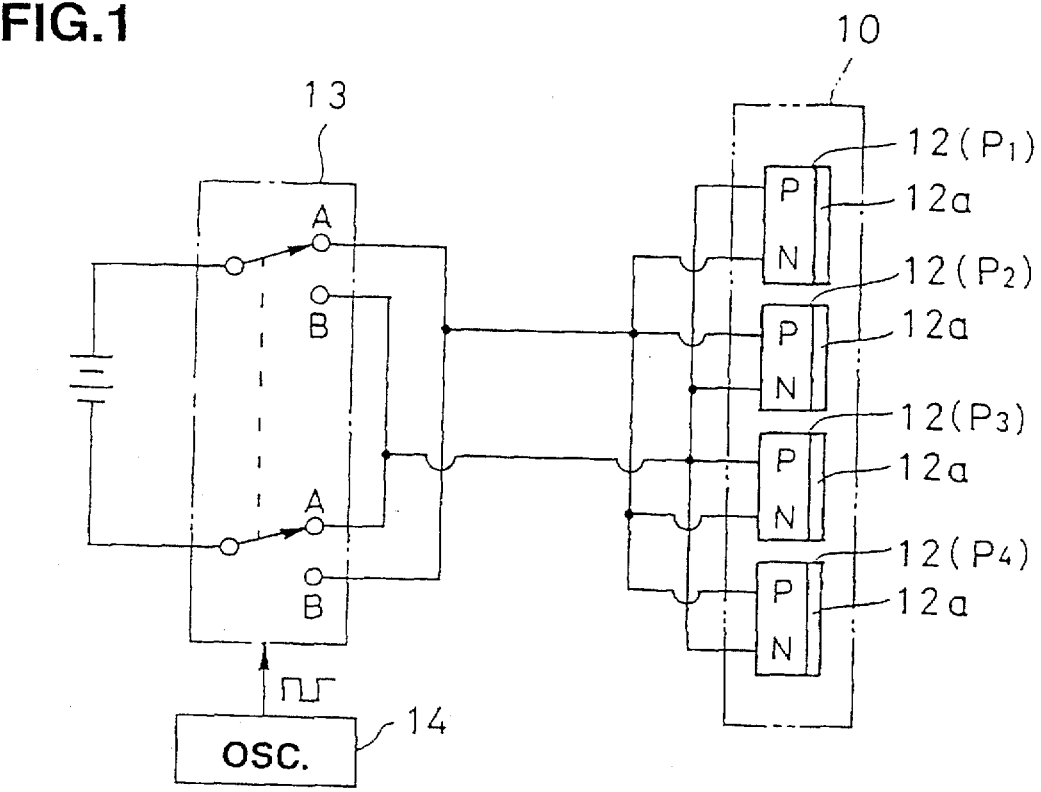
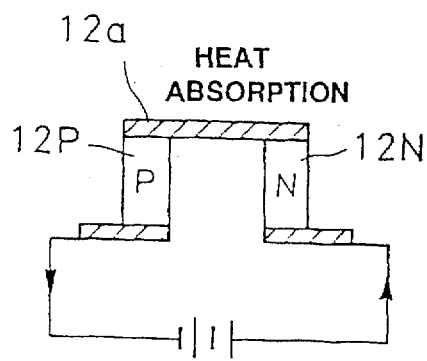
FIG.2(a)
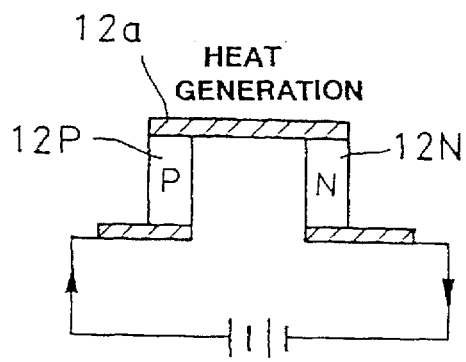
FIG.2(b)

FIG.17
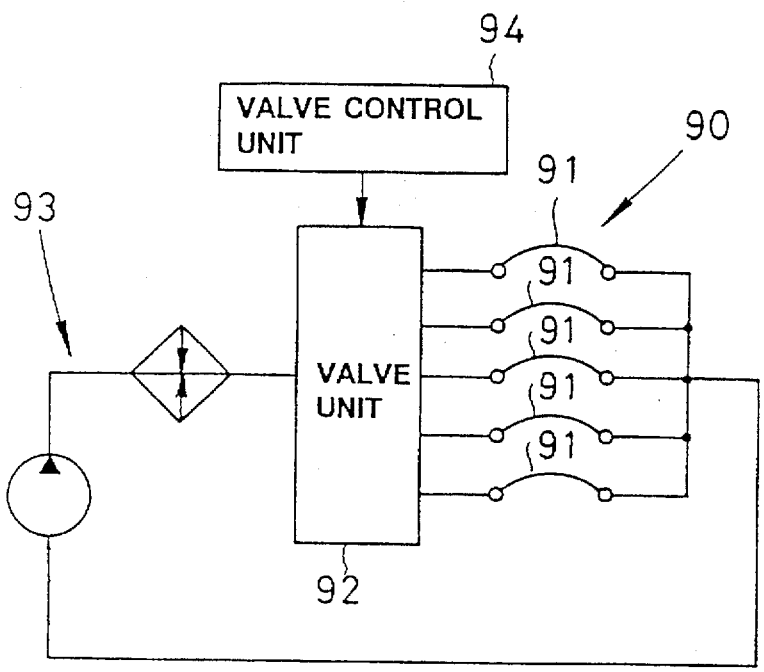
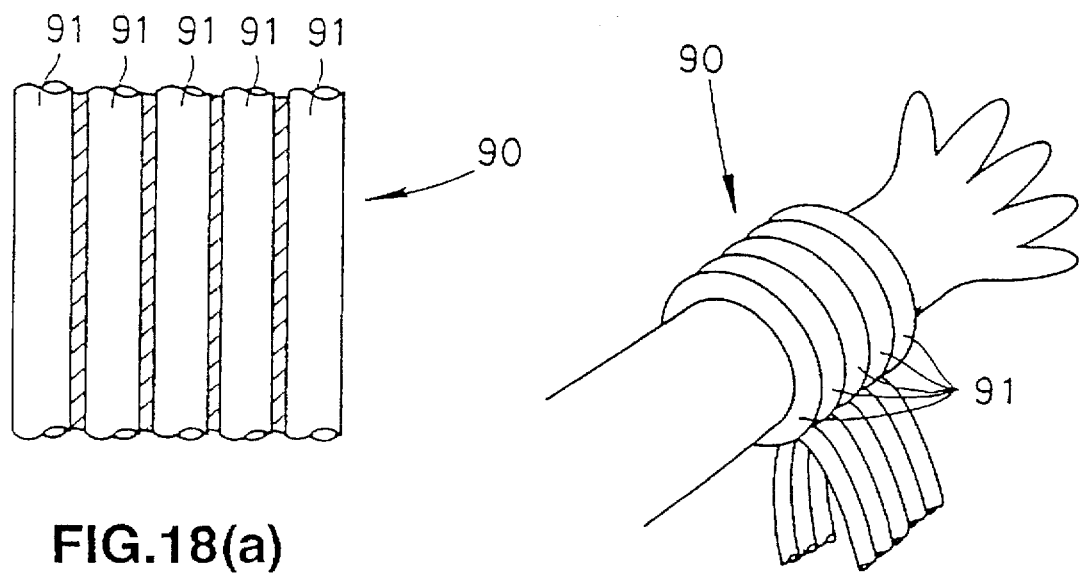
FIG.18(a)
FIG.18(b)

FIG.25

| DRIVE DATA | DRIVE ORDER (K) |
|---|---|
| A | 1→2→3→4→5→6→7→8→9→10 |
| B | 10→9→8→7→6→5→4→3→2→1 |
| C | 2→3→4→7 |
| D | 6→5→1, 2→3→4, 7→8→9→10 |
| E | 4→3→2→5→6, 10→9→8→7, 1 |
| F | 10→9→8, 4→3→2 |
| G | 8→9→10, 2→3→4 |

240

1

DEVICE FOR ACTIVATING CELLS OF A HUMAN BODY

BACKGROUND OF THE INVENTION

1. Field of the Invention

The present invention relates to a device for activating the cells of a human body by imparting stimuli.

2. Description of the Related Art

Numerous devices have hitherto been proposed for activating cells by imparting stimuli to a human body.

Such devices are, for instance, provided on the one hand with a vibrator which operates in accordance with acoustic signals emitted from an analogue disc player, digital disc player, tape-recorder or similar devices for generating acoustic signals, and on the other hand with headphones, earphones or similar means of generating audible soundwaves, and work in such a way that while the user listens to music, vibrations are imparted to the affected part in synchronism with the music.

Conventional devices of the abovementioned type all impart a continuous uniform level of stimuli to a prescribed body site. In other words, the abovementioned devices for activating cells impart a continuous uniform level of stimuli to the cells of the human body which are in contact with the vibrator.

This means there is a risk that prolonged use of this type of device may lead to acclimatization whereby the cells become insensitive to these stimuli, and it may become difficult to continue activating them.

Moreover, with this kind of cell-activating device the more the consciousness is focused on the affected part, the more it is possible to activate the cells there.

With a device like the abovementioned one where vibrations are imparted to the affected part of the human body while the user listens to music, it is possible to achieve a relaxed psychological state by listening to music while the vibrations are imparted, thus making prolonged use possible without attendant discomfort. However, because the consciousness is focused on listening to the music, which is to say it is always focused on listening to the music irrespective of differences in location of the affected part, there is a risk that the cells of the affected part will not be activated satisfactorily.

SUMMARY OF THE INVENTION

In view of the abovementioned circumstances, it is an object of the present invention to provide a device for activating the cells of a human body which enables the continuous activation of cells even during prolonged use.

It is a further object of the present invention to provide a device for activating the cells of a human body which enables the continuous activation of cells of the affected part while the consciousness is focused on that part.

To achieve the above objects, a device for activating the cells of the human body of the present invention comprises means of imparting stimuli for imparting stimuli to the human body; and means of changing the state of the stimuli for changing the state of the stimuli imparted by the means of imparting stimuli.

A device for activating the cells of the human body of the present invention also comprises means of imparting stimuli for imparting stimuli to the human body; and means of changing the location of the stimuli for changing the location of the stimuli imparted to the human body by the means of imparting stimuli.

The means of imparting preferably imparts stimuli to at least two mutually differing places in the human body, and in this case are preferably arranged in such a way that the states of the stimuli which are imparted to two mutually adjacent places on the human body are mutually opposite.

Where there is only a single means of imparting stimuli, it preferably imparts 1/f or similar irregular stimuli.

The stimuli may be imparted to the human body selectively by means of temperature, magnetism, vibration or otherwise, or by a combination of these.

Further, a device for activating the cells of the human body of the present invention comprises a mount fitted in such a way that it may be applied to and removed from the affected part of the human body; a means of imparting stimuli by vibration, which is supported by the mount and imparts stimuli to the affected part of the human body by means of vibration; and a means of generating soundwaves, which is supported by the mount and generates soundwaves to the affected part in the vicinity of the vibration element.

The means of imparting soundwaves preferably imparts stimuli by means of soundwaves with frequencies which are outside the audible frequency range, but may also make use of soundwaves with frequencies which are within the audible frequency range.

The means of imparting stimuli and the means of generating soundwaves operate in accordance with acoustic signals imparted respectively from external sources.

Because it is possible to change the state of the stimuli imparted to the human body by utilizing the means provided for that purpose, the abovementioned structure suppresses as far as possible the acclimatization to the stimuli, and allows continuous activation of cells to be achieved even during prolonged use.

Moreover, because it is possible to change the location of the stimuli imparted to the human body by utilizing the means provided for that purpose, the abovementioned structure suppresses as far as possible the acclimatization to the stimuli, and allows continuous activation of cells to be achieved even during prolonged use.

Furthermore, because the abovementioned structure allows stimulation by means of soundwaves to be imparted to an affected part of the human body in the vicinity of the affected part to which simultaneous stimulation by means of vibration is being imparted, this stimulation by soundwaves makes it feel as if the cells of the affected part were listening to the music. In this way the consciousness focuses naturally on the affected part, and it is possible to activate thoroughly the cells of the affected part while achieving a relaxed psychological state.

BRIEF DESCRIPTION OF THE DRAWINGS

FIG. 1 illustrates a first embodiment of the device for activating cells to which the present invention pertains, and is a circuitry diagram showing an example of a device which imparts stimuli to the human body by means of temperature;

FIGS. 2(a) and 2(b) are circuitry diagrams which show in concept the operational principle behind the means of imparting stimuli which is employed in the first embodiment as illustrated in FIG. 1;

FIGS. 3(a) and 3(b) are cross-sectional diagrams which show in concept the structure of the device which forms the first embodiment as illustrated in FIG. 1, while

FIG. 10(a) is a diagram which shows in concept the structure of the means of imparting stimuli which is employed in the sixth embodiment as illustrated in FIG. 9, while

FIG. 15(a) is a diagram which shows in concept the structure of the means of imparting stimuli which is employed in the eighth embodiment as illustrated in FIG. 14, while

FIG. 17 is a circuitry diagram illustrating a ninth embodiment of the device for activating cells to which the present invention pertains;

FIG. 18(a) is a diagram which shows in concept the structure of the means of imparting stimuli which is employed in the ninth embodiment as illustrated in FIG. 17, while FIG. 18(b) is a diagonal view showing in concept the device during use;

FIG. 25 is a table showing examples of the content of the memory which is employed in the device which forms the twelfth embodiment as illustrated in FIG. 24;

DESCRIPTION OF THE PREFERRED EMBODIMENTS

There follows a detailed description of the present invention with the aid of drawings which illustrate embodiments thereof.

Figure 3A:
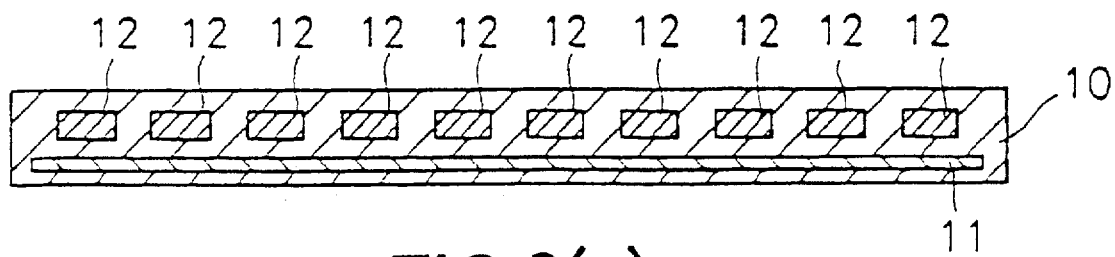
Figure 3B:
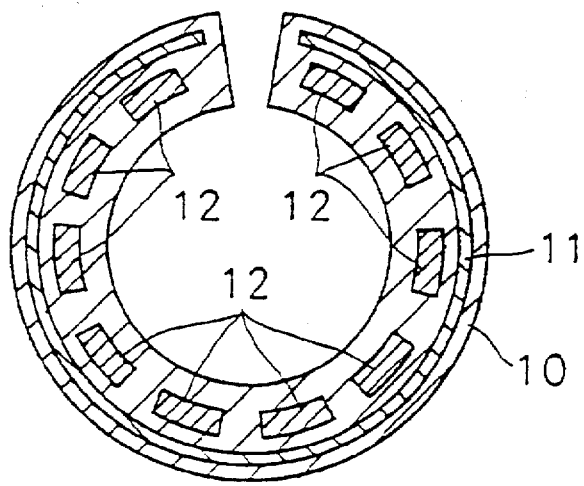
Figure 3C:
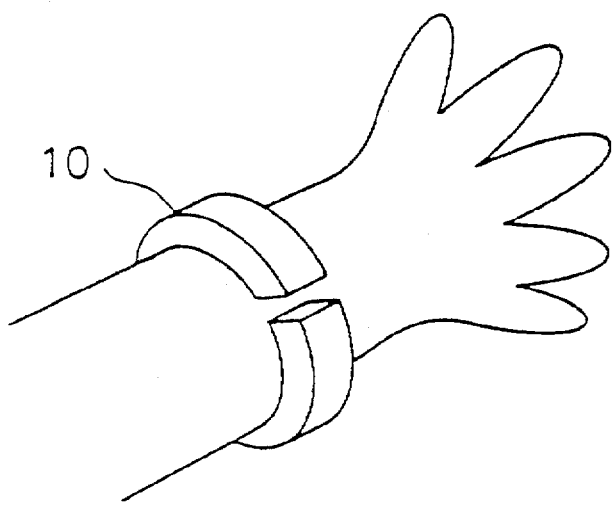
FIG. 3(c) is a diagonal view showing the device in operation.

FIGS. 1 and 3(a)–3(c) illustrate in concept a first embodiment of the device for activating cells to which the present invention pertains, and show an example of a device for activating cells which achieves cell activation in the target body by imparting stimuli to that body by means of temperature. As is shown in FIGS. 3(a)–3(c), this first embodiment has a plastic sheet 11 and a plurality of thermoelectric conversion elements 12 within a body fitment 10 which is fashioned from resin or a similar elastic and easily deformable material into the shape of a bar with a rectangular cross-section.

The plastic sheet 11 is fashioned from aluminum or a similar plastic and easily deformable material into the shape of a sheet, and is implanted on one side of the body fitment 10.

As is shown in FIGS. 2(a)–2(b), the thermoelectric conversion elements 12 utilize the Peltier effect to cause, according to the direction in which the current flows, a phenomenon of heat absorption or heat generation in the connecting metals 12a which connect the p-type semiconductors 12P and the n-type semiconductors 12N. As is shown in FIGS. 1 and 3, the connecting metals 12a are implanted in a row within the body fitment 10 in such a manner that they are close to the surface on the other side of the body fitment 10 and are facing in the same direction as one another.

As is also shown in the same drawings, these thermoelectric conversion elements 12 are connected to a power supply by way of a first switch means 13 in such a manner that the direction of the electric current in adjacent elements is mutually opposite. The first switch means 13 is driven in accordance with signals output from a variable-frequency oscillator 14, and the paired switch elements A and B are switched over in synchronization with one another according to a cycle which may be set at will in the variable-frequency oscillator.

In the device which forms the first embodiment and is configured in the abovementioned manner, if the shape of the body fitment 10 is deformed by applying external pressure, the action of the plastic sheet 11 which is implanted within it allows the body fitment 10 to be retained in the deformed state. Thus, if the body fitment 10 is suitably bent in such a manner that the connecting metals 12a all face inward as is shown in FIG. 3(b), it is possible without difficulty to wind the device for activating cells around a body part in such a manner that the connecting metals 12a are each in close proximity to the cells which it is desired to activate, as shown in FIG. 3(c).

Figure 4A:
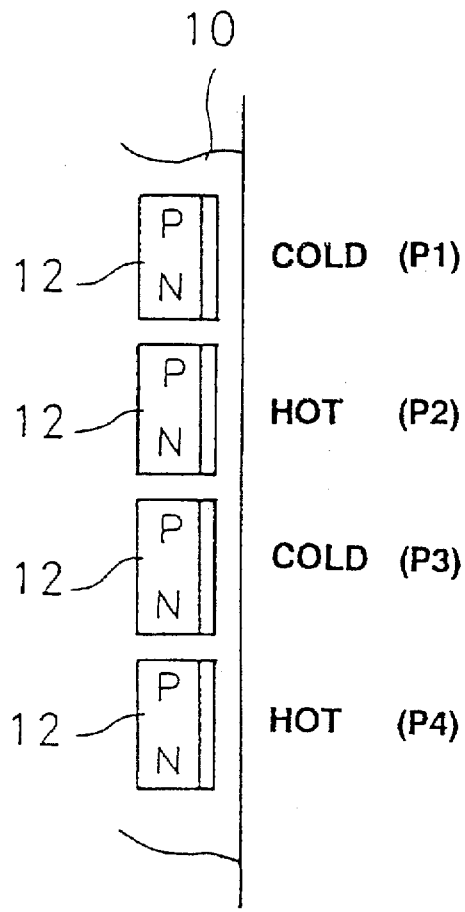
FIGS. 4(a) and 4(b) are cross-sectional diagrams which show in concept the action of the device which forms the first embodiment as illustrated in FIG. 1.

Now, if the first switch means 13 is in the state shown in FIG. 1, which is to say if the pair of switch elements A is each connected to its contact, and forward voltage is applied to the thermoelectric conversion elements 12 located at P2 and P4, the phenomenon of heat generation is triggered in the connecting metals 12a of the thermoelectric conversion elements 12 located at P2 and P4. Meanwhile, reverse voltage is applied to the thermoelectric conversion elements 12 located at P1 and P3, and the phenomenon of heat absorption is triggered in the connecting metals 12a of the thermoelectric conversion elements 12 located at P1 and P3. Consequently, as is shown in FIG. 4(a), high-temperature stimuli are imparted to the cells at sites corresponding to P2 and P4, while low-temperature stimuli are imparted to the cells at sites corresponding to P1 and P3, thus activating the cells at the sites corresponding to P1, P2, P3 and P4 as well as between them.

Figure 4B:
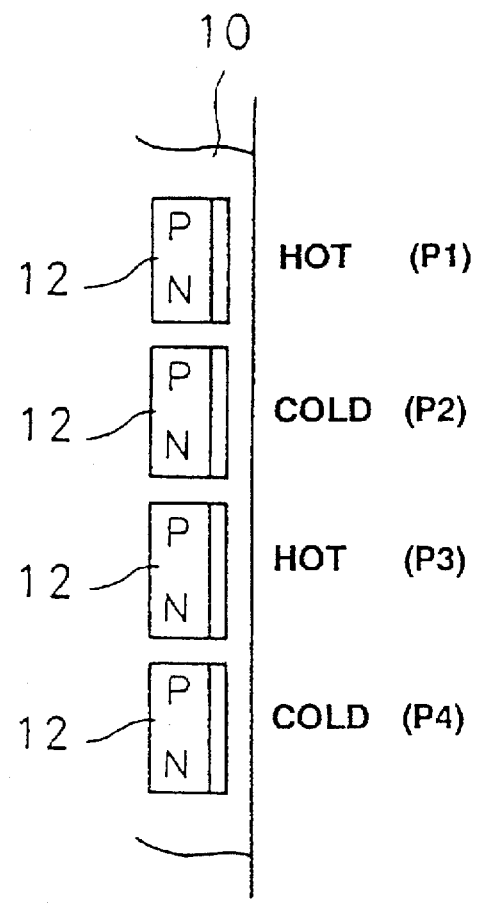

On the other hand, if the first switch means 13 is switched over from the state shown in FIG. 1 in accordance with a signal output from the variable-frequency oscillator 14, which is to say if the pair of switch elements B is each connected to its contact, reverse voltage is applied to the thermoelectric conversion elements 12 located at P2 and P4, the phenomenon of heat absorption is triggered in the connecting metals 12a of the thermoelectric conversion elements 12 located at P2 and P4. Meanwhile, forward voltage is applied to the thermoelectric conversion elements 12 located at P1 and P3, and the phenomenon of heat generation is triggered in the connecting metals 12a of the thermoelectric conversion elements 12 located at P1 and P3. Consequently, as is shown in FIG. 4(b), low-temperature stimuli are imparted to the cells at the sites corresponding to P2 and P4, while high-temperature stimuli are imparted to the cells at the sites corresponding to P1 and P3, thus activating the cells at the sites corresponding to P1, P2, P3 and P4 as well as between them.

Because of the considerable difference in temperature at each site as the state of the stimulus reverses from hot to cold and from cold to hot, the degree of stimulation which is imparted to the cells increases, and activation of the cells becomes marked.

Then, because the phenomena of heat generation and heat absorption are triggered repeatedly in each of the thermoelectric conversion elements 12 in accordance with signals output from the variable-frequency oscillator 14, and the state of the temperature stimuli imparted from these thermoelectric conversion elements 12 changes cyclically from hot to cold, the device which forms the first embodiment prevents as far as possible the acclimatization to the stimuli, and allows continuous activation of cells to be achieved even during prolonged use.

Figure 5:
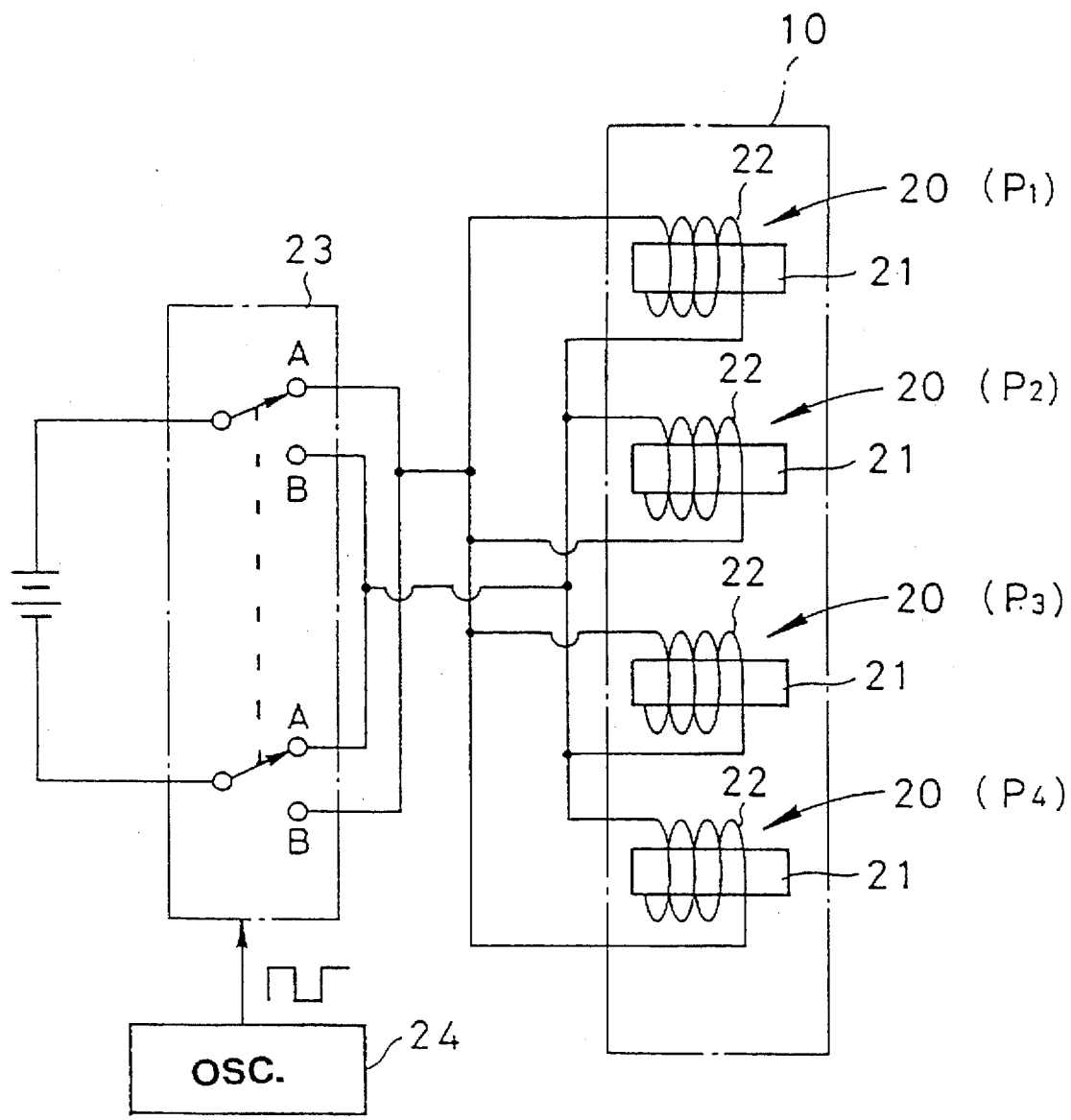
FIG. 5 illustrates a second embodiment of the device for activating cells to which the present invention pertains, and is a circuitry diagram showing an example of a device which imparts stimuli to the human body by means of magnetism.
Figure 6:
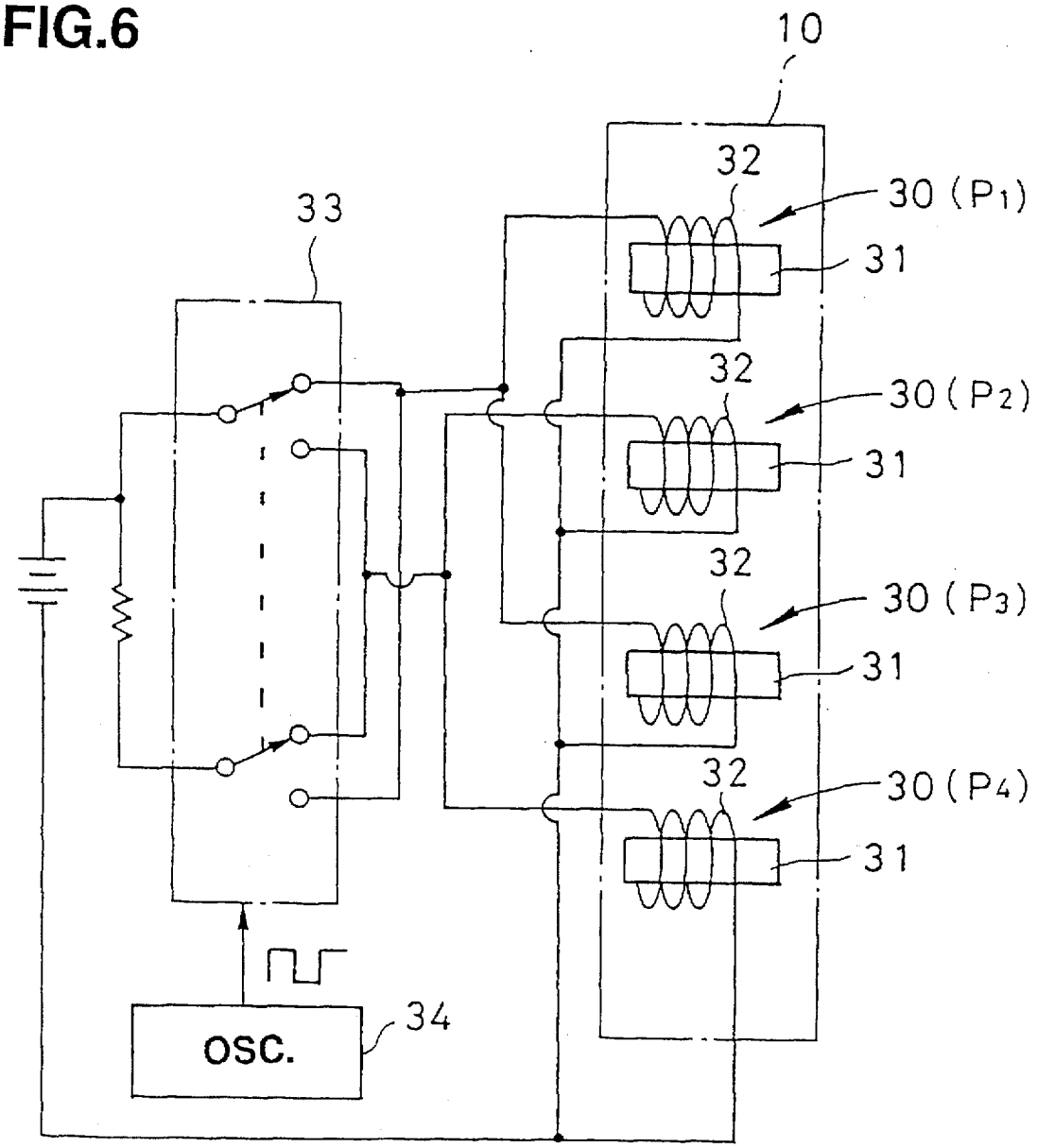
FIG. 6 illustrates a third embodiment of the device for activating cells to which the present invention pertains, and is a circuitry diagram showing a variant example of a device which imparts stimuli to the human body by means of magnetism.

FIGS. 5 and 6 illustrate in concept respectively second and third embodiments of the device for activating cells to which the present invention pertains. The devices which form the second and third embodiments achieve cell activation in the target body by imparting stimuli to that body by means of magnetism. Instead of the thermoelectric conversion elements 12 of the device which forms the first embodiment as illustrated in FIG. 1, they have respectively a plurality of electromagnets 20 and 30 within the body fitment 10 inside which is the plastic sheet 11, which is to say they have cores 21 and 31 consisting of magnetic bodies around which are wound coils 22 and 32.

Firstly, in the device which forms the second embodiment as illustrated in FIG. 5, the electromagnets 20 are connected to a power supply by way of a second switch means 23 in such a manner that the direction of the electric current to the coils 22 of adjacent electromagnets is mutually opposite.

If the device which forms this second embodiment is in the state shown in FIG. 5, which is to say if the switch elements A are each connected to their contact, and a left-handed electric current flows through the coils 22 of the electromagnets 20 located at P2 and P4 towards the tips of their respective cores 21, a magnetic field is generated whereof the tips of the cores 21 located at P2 and P4 form S poles. Meanwhile, a right-handed electric current flows through the coils 22 of the electromagnets 20 located at P1 and P3 towards the tips of their respective cores 21, and a magnetic field is generated whereof the tips of the cores 21 located at P1 and P3 form N poles. On the other hand, if the second switch means 23 is switched over in accordance with a signal output from the variable-frequency oscillator 24, which is to say if the switch elements B are each connected to their contact, and a right-handed electric current flows through the coils 22 of the electromagnets 20 located at P2 and P4 towards the tips of their respective cores 21, a magnetic field is generated whereof the tips of the cores 21 located at P2 and P4 form N poles. Meanwhile, a left-handed electric current flows through the coils 22 of the electromagnets 20 located at P1 and P3 towards the tips of their respective cores 21, and a magnetic field is generated whereof the tips of the cores 21 located at P1 and P3 form S poles.

Then, because opposite magnetic fields are triggered repeatedly in the cores 21 of each of the electromagnets 20 in accordance with signals output from the variable-frequency oscillator 24, and the state of the magnetic stimuli imparted from these electromagnets 20 changes cyclically, the device which forms the second embodiment prevents as far as possible the acclimatization to the stimuli, and allows continuous activation of cells to be achieved even during prolonged use.

On the other hand, in the device which forms the third embodiment as illustrated in FIG. 6, the electromagnets 30 are connected to a power supply by way of a third switch means 33 in such a manner that the magnitude of the electric current to the coils 32 of adjacent electromagnets is mutually different.

If the device which forms this third embodiment is in the state shown in FIG. 6, which is to say if the switch elements A are each connected to their contact, and the electric current which flows through the coils 32 located at P2 and P4 is smaller than that which flows through the coils 32 located at P1 and P3, a relatively weak magnetic field is generated in the coils 32 located at P2 and P4, while a relatively strong magnetic field is generated in the coils 32 located at P1 and P3. On the other hand, if the third switch means 33 is switched over-in accordance with a signal output from the variable-frequency oscillator 34, which is to say if the switch elements B are each connected to their contact, and the electric current which flows through the coils 32 located at P1 and P3 is smaller than the one which flows through the coils 32 located at P2 and P4, a relatively weak magnetic field is generated in the coils 32 located at P1 and P3, while a relatively strong magnetic field is generated in the coils 32 located at P2 and P4.

Then, because strong or weak magnetic fields are triggered repeatedly in the each of the electromagnets 30 in accordance with signals output from the variable-frequency oscillator 34, and the state of the magnetic stimuli imparted from these electromagnets 20 changes cyclically from strong to weak, the device which forms the third embodiment prevents as far as possible the acclimatization to the stimuli, and allows continuous activation of cells to be achieved even during prolonged use.

The devices which form the second and third embodiments are configured in such a manner that magnetic stimuli are imparted to the human body by means of the electromagnets 20 and 30. However, it is also possible to impart stimuli to the human body by means of permanent magnets. That is to say, if the permanent magnets are located in such a manner that they are able to rotate and it is possible to change the direction of the magnetic field by rotating them cyclically as desired, and if a movable screen is located between the permanent magnets and the human body and is moved cyclically as desired, it is possible to modify the magnetic field from strong to weak according to the presence or absence of the screen.

Figure 7:
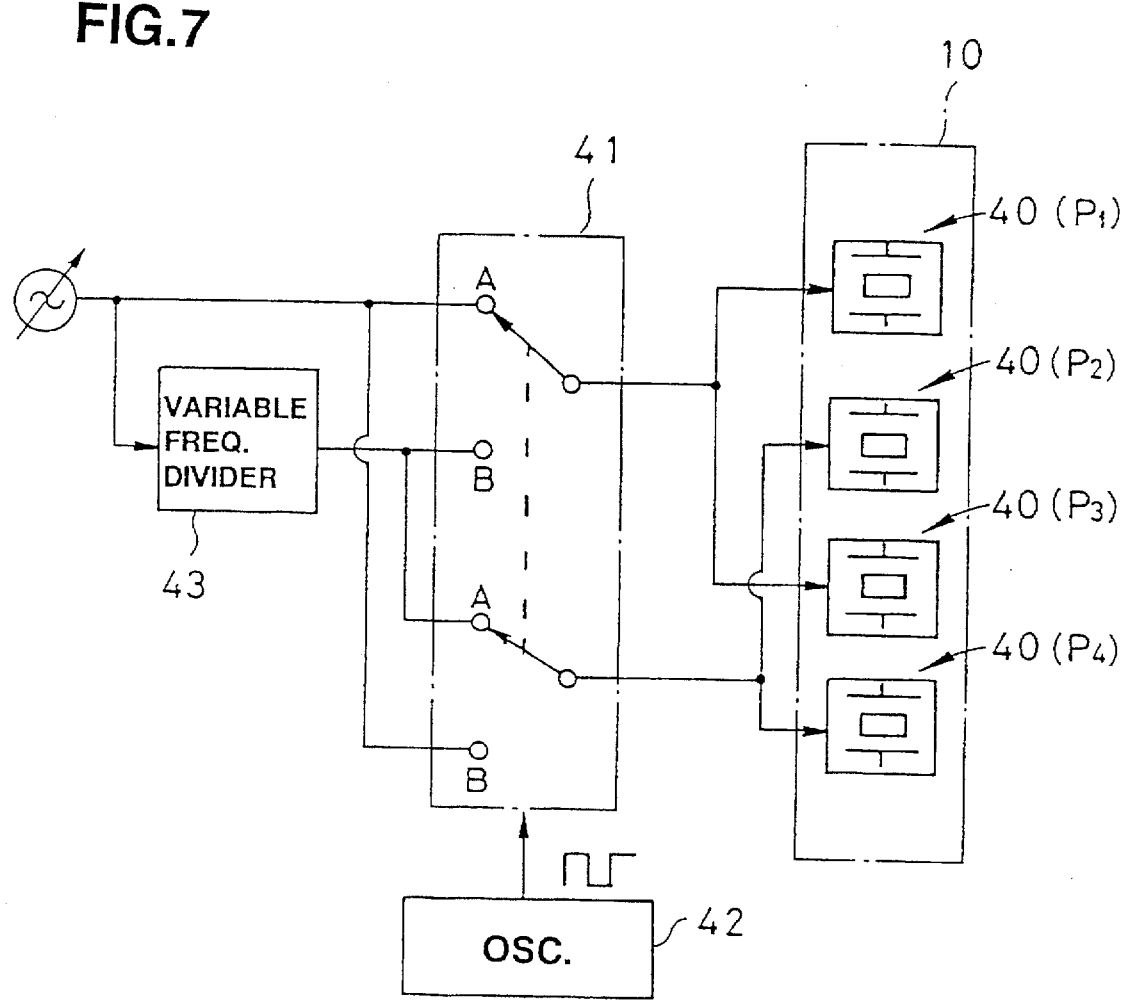
FIG. 7 illustrates a fourth embodiment of the device for activating cells to which the present invention pertains, and is a circuitry diagram showing an example of a device which imparts stimuli to the human body by means of vibration.
Figure 8:
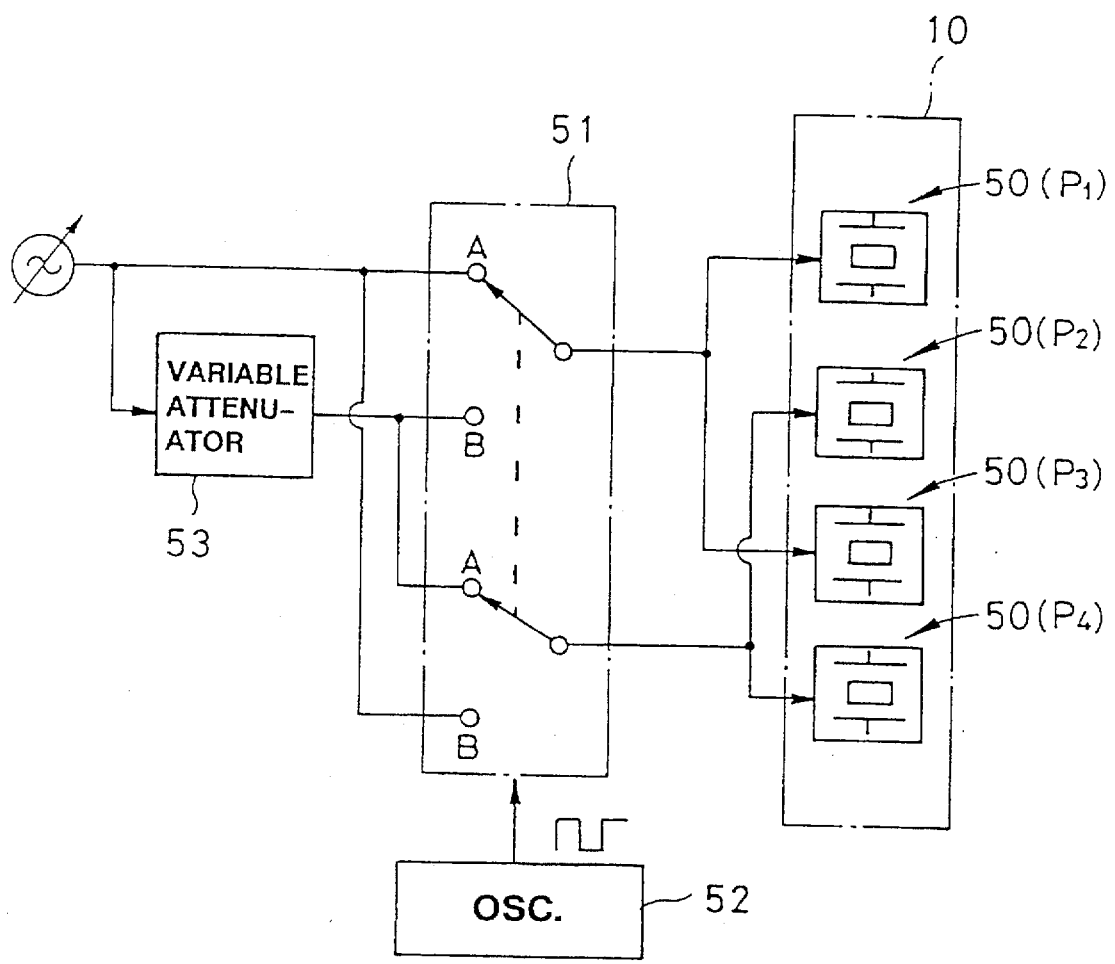
FIG. 8 illustrates a fifth embodiment of the device for activating cells to which the present invention pertains, and is a circuitry diagram showing a variant example of a device which imparts stimuli to the human body by means of vibration.

FIGS. 7 and 8 illustrate in concept respectively a fourth and fifth embodiment of the device for activating cells to which the present invention pertains. The devices which form these fourth and fifth embodiments achieve cell activation in the target body by imparting stimuli to that body by means of vibration. Instead of the thermoelectric conversion elements 12 of the device which forms the first embodiment as illustrated in FIG. 1, they have respectively a plurality of piezoelectric vibration elements 40 and 50 of crystal, potassium sodium tartrate (Rochelle salt), ammonium dihydrogen phosphate (ADP), barium titanate or similar porcelain within the body fitment 10 inside which is the plastic sheet 11.

Firstly, in the device which forms the fourth embodiment as illustrated in FIG. 7, the piezoelectric vibration elements 40 are connected to an alternating power supply by way of a fourth switch means 41 in such a manner that the frequencies of the voltage imparted to adjacent piezoelectric vibration elements are mutually different.

If the device which forms this fourth embodiment is in the state shown in FIG. 7, which is to say if the switch elements A are each connected to their contact, and the frequency of the alternating voltage which is applied by the action of the variable frequency divider 43 to the piezoelectric vibration elements 40 located at P2 and P4 is lower than the frequency of the alternating voltage which is applied to the piezoelectric vibration elements 40 located at P1 and P3, vibrations of a relatively low frequency are generated in the piezoelectric vibration elements 40 located at P2 and P4, while vibrations of a relatively high frequency are generated in the piezoelectric elements 40 located at P1 and P3. On the other hand, if the fourth switch means 41 is switched over in accordance with a signal output from the variable-frequency oscillator 42, which is to say if the switch elements B are each connected to their contact, and the frequency of the alternating voltage which is applied by the action of the variable frequency divider 43 to the piezoelectric vibration elements 40 located at P1 and P3 is lower than the frequency of the alternating voltage which is applied to the piezoelectric vibration elements 40 located at P2 and P4, vibrations of a relatively high frequency are generated in the piezoelectric vibration elements 40 located at P2 and P4, while vibrations of a relatively low frequency are generated in the piezoelectric elements 40 located at P1 and P3.

Then, because vibrations of differing frequency are triggered repeatedly in the piezoelectric vibration elements 40 in accordance with signals output from the variable-frequency oscillator 42, and the state of the vibratory stimuli imparted from these piezoelectric vibration elements 40 changes cyclically from strong to weak, the device which forms the fourth embodiment prevents as far as possible the acclimatization to the stimuli, and allows continuous activation of cells to be achieved even during prolonged use.

In the device which forms the fifth embodiment as illustrated in FIG. 8, the piezoelectric vibration elements 50 are connected to an alternating power supply by way of a fifth switch means 51 in such a manner that the amplitude of the voltage imparted to adjacent piezoelectric vibration elements is mutually different.

If the device which forms this fifth embodiment is in the state shown in FIG. 8, which is to say if the switch elements B are each connected to their contact, and the amplitude of the alternating voltage which is applied by the action of the variable attenuator 53 to the piezoelectric vibration elements 50 located at P2 and P4 is lower than the amplitude of the alternating voltage which is applied to the piezoelectric vibration elements 50 located at P1 and P3, relatively weak vibrations are generated in the piezoelectric vibration elements 50 located at P2 and P4, while relatively strong vibrations are generated in the piezoelectric elements 50 located at P1 and P3. On the other hand, if the fifth switch means 51 is switched over in accordance with a signal output from the variable-frequency oscillator 52, which is to say if the switch elements Bare each connected to their contact, and the amplitude of the alternating voltage which is applied by the action of the variable attenuator 53 to the piezoelectric vibration elements 50 located at P1 and P3 is lower than the amplitude of the alternating voltage which is applied to the piezoelectric vibration elements 50 located at P2 and P4, relatively strong vibrations are generated in the piezoelectric vibration elements 50 located at P2 and P4, while relatively weak vibrations are generated in the piezoelectric elements 50 located at P1 and P3.

Then, because vibrations of differing amplitude are triggered repeatedly in the piezoelectric vibration elements 50 in accordance with signals output from the variable-frequency oscillator 52, and the state of the vibratory stimuli imparted from these piezoelectric vibration elements 50 changes cyclically from strong to weak, the device which forms the fifth embodiment prevents as far as possible the acclimatization to the stimuli, and allows continuous activation of cells to be achieved even during prolonged use.

Figure 9:
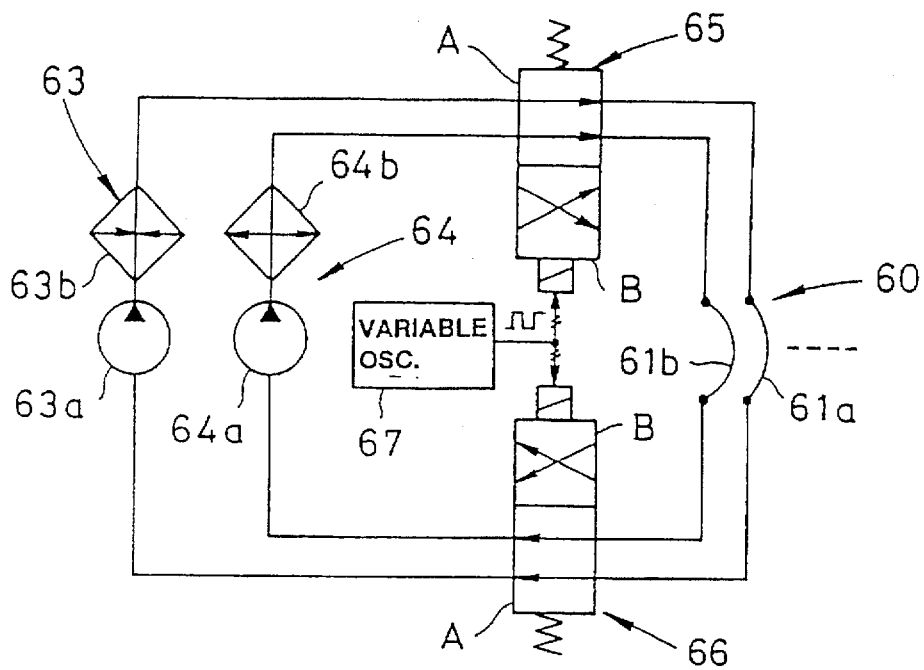
FIG. 9 illustrates a sixth embodiment of the device for activating cells to which the present invention pertains, and is a circuitry diagram showing an example of a device which imparts stimuli to the human body by means of temperature.

FIGS. 9 and 10 illustrate in concept a sixth embodiment of the device for activating cells to which the present invention pertains, and show an example of a device for activating cells which achieves cell activation in the target body by imparting stimuli to that body by means of temperature.

As is shown in FIGS. 10(a)–10(d), this sixth embodiment has a body fitment 60 which is fashioned from resin or a similar elastic and easily deformable material. The body fitment 60 is formed by connecting the circumferences of a pair of tubes 61 to one another, and supports on its circumference a plurality of contact bodies 62. The contact bodies 62 comprise a contact member 62a which is long enough to connect the circumferences of the pair of tubes 61, a shaft member 62b which protrudes from a position on the contact member 62 corresponding to one of the tubes 61 in such a manner that its tip penetrates within that tube 61, and a thermal conduction member 62c which projects laterally from the tip of the shaft member 62b. The shaft members 62b are arranged on the body fitment 60 in a zigzag fashion, which is to say in such as manner that the thermal conduction members 62c of adjacent contact bodies 62 are held within mutually differing tubes 61.

As is shown in FIG. 9, this device which forms the sixth embodiment has a means of supplying hot water 63 and a means of supplying cold water 64. The means of supplying hot water 63 consists of a pump 63a and a heater 63b, while the means of supplying cold water 64 consists of a pump 64a and a cooler 64b. They are each connected selectively by way of electromagnetic switch-over valves 65 and 66 to the pair of tubes 61, and are driven in synchronization with one another in accordance with signals output from the variable-frequency oscillator 67, the switch-over being implemented according to a cycle which may be set at will in the variable-frequency oscillator 67.

Figure 10A:
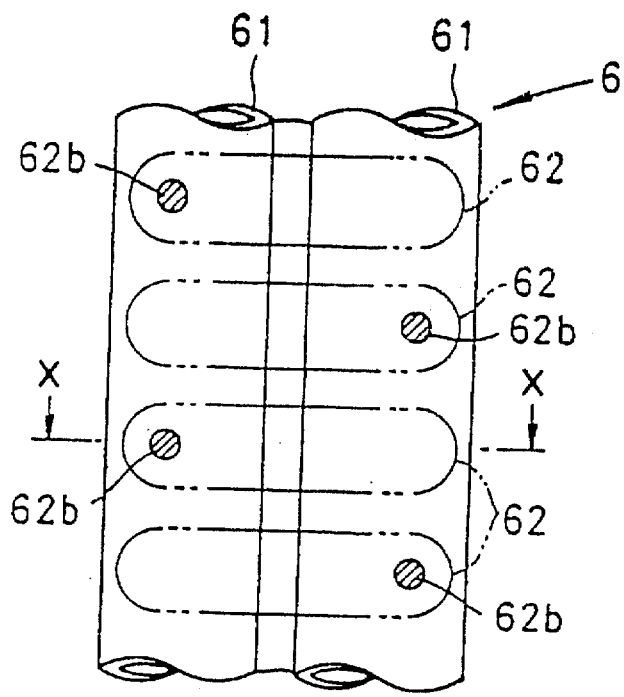
Figure 10B:
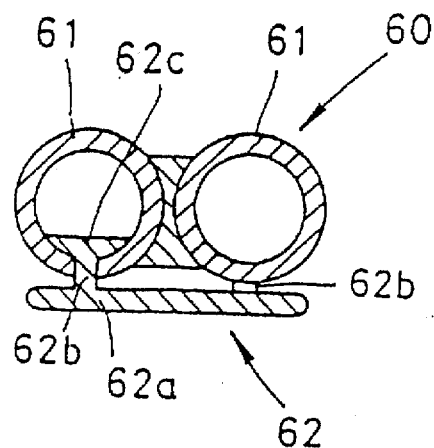
FIG. 10(b) is a cross-sectional diagram along line X—X in FIG. 10(a)
Figure 10C:
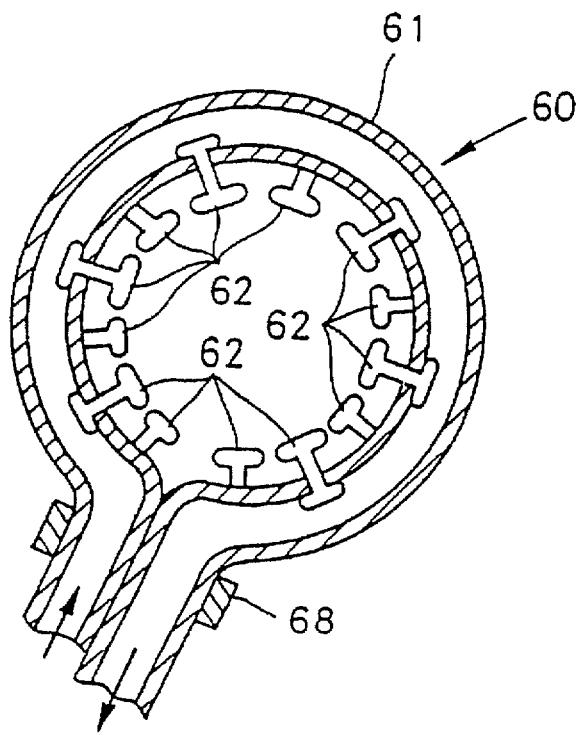
FIG. 10(c) is a cross-sectional diagram showing in concept the device during use.
Figure 10D:
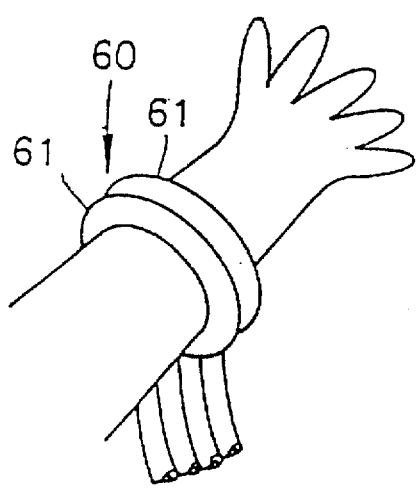
FIG. 10(d) is a diagonal view showing in concept the device during use.

As is shown in FIGS. 10(c) and 10(d), the shape of the device which forms the sixth embodiment and is configured in the abovementioned manner can be changed by applying external pressure to the body fitment with the contact bodies 62 on the inside. Moreover, by fastening the ends of the body fitment 60 together by means of the fastener 68 the body fitment can be held in such a manner that the contact members 62a of the contact bodies 62 are each in contact with the cells which it is desired to activate.

Now, if the pair of switch-over valves 65 and 66 are both demagnetized and the pair of tubes 61 is connected by way of the first position A to the means of supplying hot water 63 and the means of supplying cold water 64 respectively, hot water is supplied to one of the tubes (hereinafter referred to as the first tube 61a), and the temperature of the contact body 62 of which the thermal conduction member 62c is held within the first tube 61a rises thanks to the hot water. Meanwhile, cold water is supplied the other tube (hereinafter referred to as the second tube 61b), and the temperature of the contact body 62 of which the thermal conduction member 62c is held within the second tube 61b falls thanks to the cold water. Consequently, high-temperature stimuli are imparted to cells in sites which are in contact with contact bodies 62 wherein the temperature has risen, while cold-temperature stimuli are imparted to the cells in sites which are in contact with contact bodies 62 wherein the temperature has fallen, thus activating the respective cells in these sites and between them.

On the other hand, if the pair of electromagnetic switch-over valves 65 and 66 is switched over from the state shown in FIG. 9 in accordance with a signal output from the variable-frequency oscillator 67, which is to say if the pair of electromagnetic switch-over valves 65 and 66 is excited and the pair of tubes 61 is connected by way of the second position B to the means of supplying hot water 63 and the means of supplying cold water 64 respectively, cold water is supplied to the first tube 61a, and the temperature of the contact body 62 of which the thermal conduction member 62c is held within the first tube 61a falls thanks to the cold water. Meanwhile, hot water is supplied the second tube 61b, and the temperature of the contact body 62 of which the thermal conduction member 62c is held within the second tube 61b rises thanks to the hot water. Consequently, high-temperature stimuli are imparted to cells in sites which are in contact with contact bodies 62 wherein the temperature has risen, while cold-temperature stimuli are imparted to the cells in sites which are in contact with contact bodies 62 wherein the temperature has fallen, thus activating the respective cells in these sites and between them.

Because of the considerable difference in temperature at each abovementioned site as the state of the stimulus reverses from hot to cold and from cold to hot, the degree of stimulation which is imparted to the cells increases, and activation of the cells becomes marked.

Then, because hot and cold water is supplied selectively to the first tube 61a and the second tube 61b in accordance with signals output from the variable-frequency oscillator 67, triggering repeated rises and falls in temperature in the contact bodies 62 which are held in the tubes 61a and 61b in such a manner that the state of the temperature stimuli imparted from these contact bodies 62 changes cyclically from hot to cold, the device which forms the sixth embodiment prevents as far as possible the acclimatization to the stimuli, and allows continuous activation of cells to be achieved even during prolonged use.

In the device which forms the sixth embodiment, water is supplied to the tubes 61, but it is possible to supply oil and other liquids or air and other gases instead of water.

Figure 11:
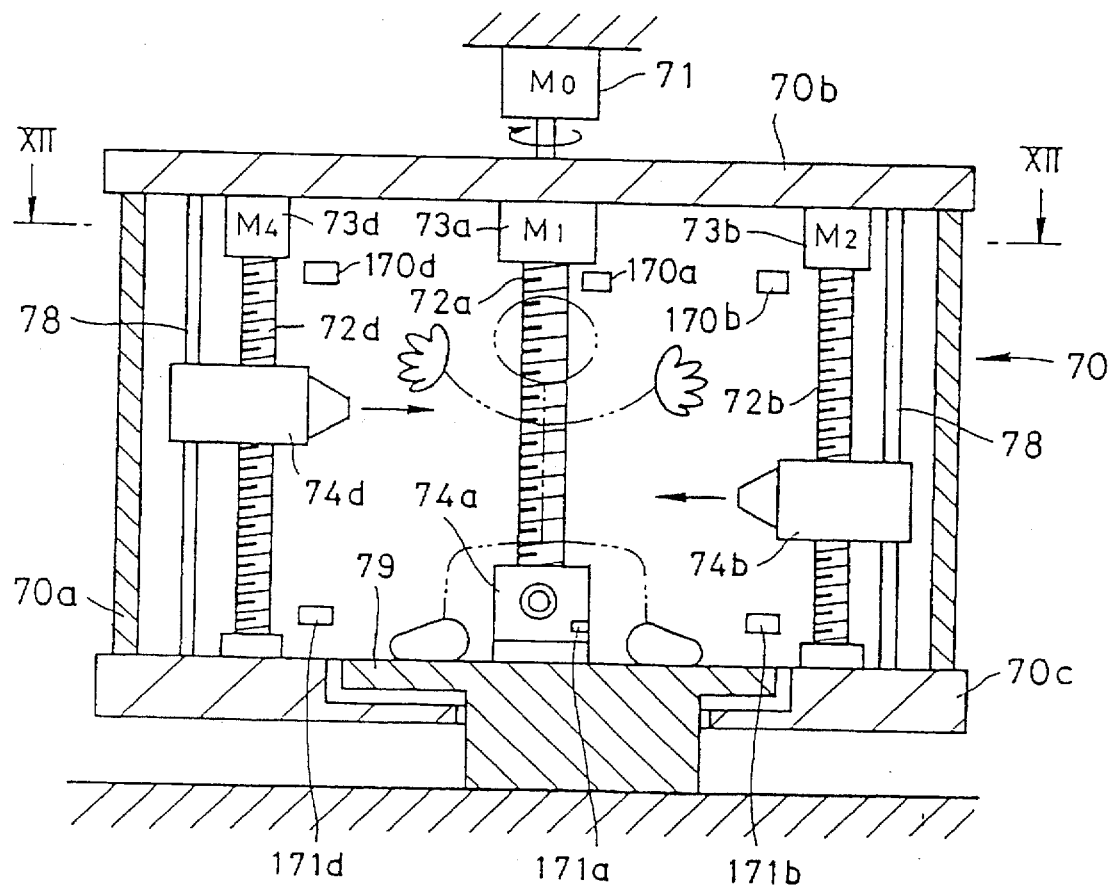
FIG. 11 illustrates a seventh embodiment of the device for activating cells to which the present invention pertains, and is a cross-sectional diagram showing an example of a device which imparts stimuli to the human body by means of temperature.
Figure 12:
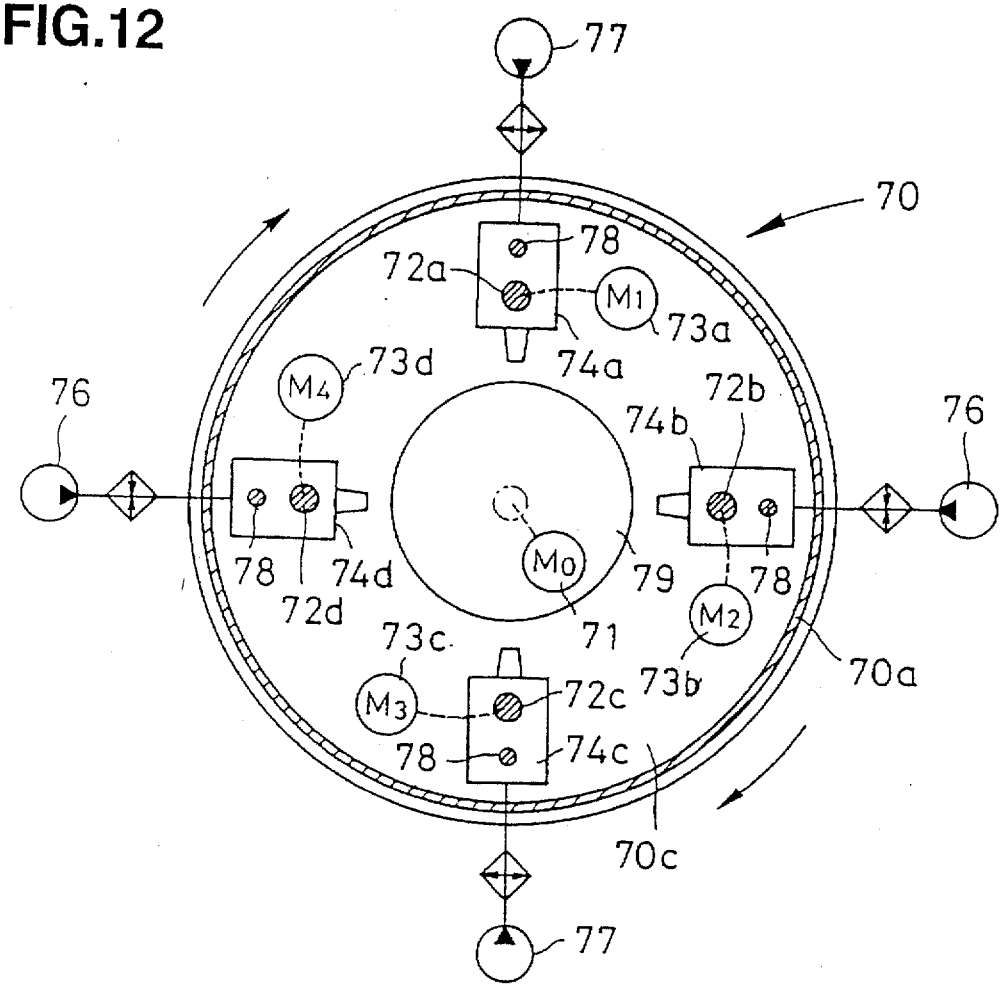
FIG. 12 is a cross-sectional diagram along line XII—XII in FIG. 11.
Figure 13:
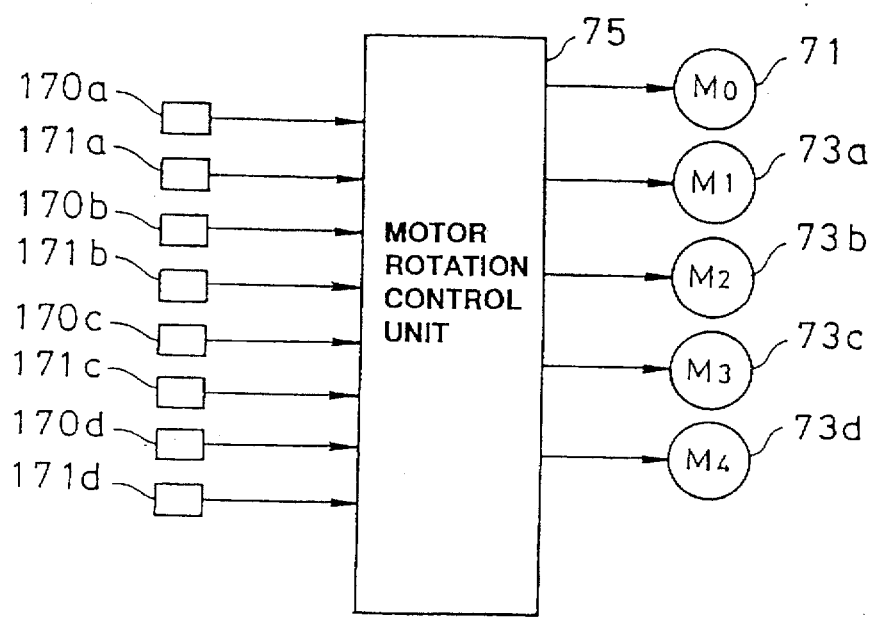
FIG. 13 is a block diagram showing the drive circuitry of the means of changing the location of stimuli which is employed in the device which forms the seventh embodiment as illustrated in FIG. 11.

FIGS. 11–13 illustrate in concept a seventh embodiment of the device for activating cells to which the present invention pertains, and show an example of a device for activating cells which achieves cell activation in the target body by imparting stimuli to that body by means of temperature.

As is shown in FIGS. 11 and 12, the device which forms this seventh embodiment is provided with a tubular chamber 70. The chamber 70 has peripheral walls 70a, a top wall 70b and a bottom wall 70c, and is driven by the principal driving motor 71, which is connected to the center part of the top wall 70b, in such a manner as to rotate around a vertical axis. The chamber 70 also has four screw rods 72a, 72b, 72c and 72d between the top wall 70b and the bottom wall 70c. The screw rods 72a, 72b, 72c and 72d stretch in a vertical direction, and each is fitted in such a manner that it is capable of rotating around its own axis. They are equipped at their respective top ends with position-changing motors 73a, 73b, 73c and 73d, while each of the shafts is fitted with a nozzle body 74a, 74b, 74c and 74d respectively.

As is shown in FIGS. 11 and 12, the nozzle bodies 74a, 74b, 74c and 74d spray liquid from nozzles fitted on their respective tips, the nozzles being fitted more or less horizontally on to the screw rods 72a, 72b, 72c and 72d in such a manner that they face towards the center of the chamber 70. As is clear from FIG. 12, to these nozzle bodies 74a, 74b, 74c and 74d are connected alternate separate hot water supply pumps 76 and cold water supply pumps 77, while slide rods 78 pass through the outer ends of each of them parallel to the screw rods 72a, 72b, 72c and 72d.

Furthermore, as is shown in FIG. 11, the device which forms the seventh embodiment is fitted with pairs of limit sensors 170a, 171a, 170b, 171b, 170c, 171c, 170d and 171d in positions which correspond respectively to those in which the screw rods 72a, 72b, 72c and 72d are fitted within the chamber 70. The limit sensors 170a, 171a, 170b, 171b, 170c, 171c, 170d and 171d comprise proximity switches, photoelectric switches or similar suitable switch means, and are fitted respectively at the top and bottom ends of the screw rods 72a, 72b, 72c and 72d, operating in such a manner that they impart an output signal to the motor rotation control unit 75 at such time as the nozzle bodies 74a, 74b, 74c and 74d are positioned at the upper or lower limits in relation to the screw rods 72a, 72b, 72c and 72d.

Moreover, the chamber 70 is structured in such a manner that there is in the center of the bottom wall 70c a fixed floor 79 which does not rotate.

In the device which forms the seventh embodiment and is configured as described above, operating the position-changing motors 73a, 73b, 73c and 73d which are connected respectively to the screw rods 72a, 72b, 72c and 72d causes the respective nozzle bodies 74a, 74b, 74c and 74d to move in a vertical direction upwards and downwards. Each of the position-changing motors 73a, 73b, 73c and 73d is controlled by the motor rotation control unit 75 in accordance with signals output from the limit sensors 170a, 171a, 170b, 171b, 170c, 171c, 170d and 171d in such a manner that the corresponding nozzle bodies 74a, 74b, 74c and 74d move up and down between the upper and lower positions. If then the principal driving motor 71 is operated, the chamber 70 with the screw rods 72a, 72b, 72c and 72d rotates around a vertical axis, with the result that the nozzle bodies 74a, 74b, 74c and 74d each moves in a spiral course in relation to the fixed floor 79.

Consequently, if a person is made to stand on the fixed floor 79 in the center of the chamber 70 and the position-changing motors 73a, 73b, 73c and 73d are each operated together with the principal driving motor 71 and the hot water supply pumps 76 and cold water supply pumps 77, because hot and cold water are respectively sprayed in a spiral pattern on to the person standing on the fixed floor 79 in such a manner that hot and cold water stimuli are each imparted cyclically to the cells, the position changing continuously, the device which forms the seventh embodiment prevents as far as possible the acclimatization to the stimuli, and allows continuous activation of cells to be achieved even during prolonged use.

In the device which forms the seventh embodiment, water is sprayed from the nozzles, but it is also possible to spray other liquids or air. Moreover, there is no absolute need to operate the principal driving motor 71 and the position-changing motors 73a, 73b, 73c and 73d continuously, it being possible to achieve the same effect by operating them intermittently. Nor is there is any need to operate both the principal driving motor 71 and the position-changing motors 73a, 73b, 73c and 73d, it being possible to move each of the nozzle bodies 74a, 74b, 74c and 74d simply upwards and downwards by means of the position-changing motors 73a, 73b, 73c and 73d, and by means of the principal driving motor 71 to move them simply in the direction of the rotation. In such cases, there is no absolute need to move the nozzle bodies 74a, 74b, 74c and 74d cyclically, it being possible to achieve the same effect by moving them at random.

Figure 14:
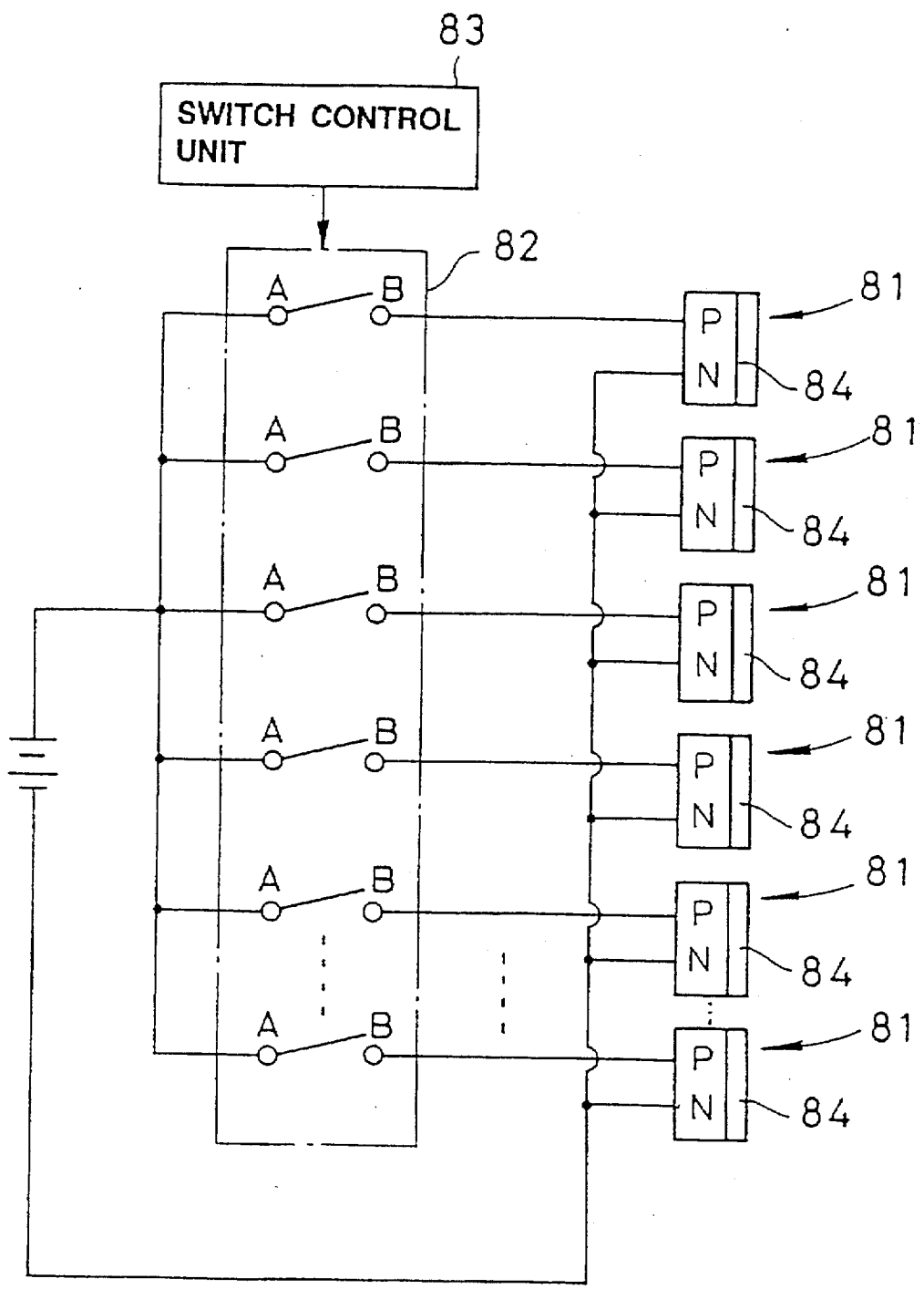
FIG. 14 is a circuitry diagram illustrating an eighth embodiment of the device for activating cells to which the present invention pertains.

FIGS. 14–16 illustrate in concept an eighth embodiment of the device for activating cells to which the present invention pertains, and show an example of a device for activating cells which achieves cell activation in the target body by imparting stimuli to that body by means of temperature.

Figure 15A:
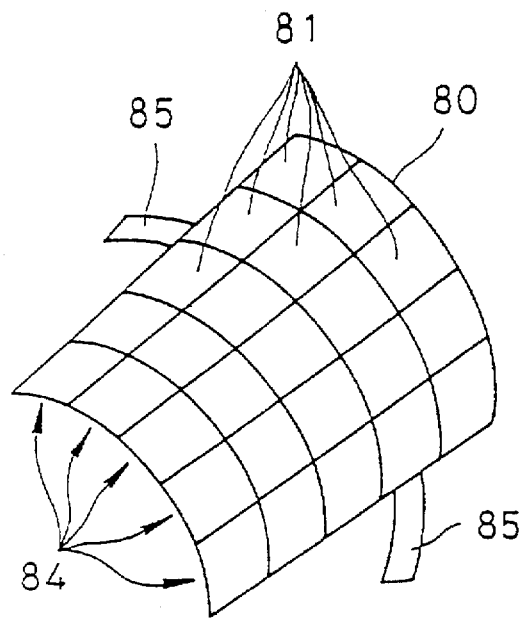
Figure 15B:
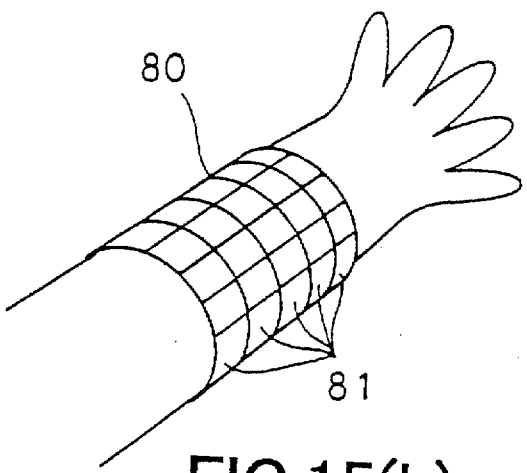
FIG. 15(b) is a diagonal view showing in concept the device during use.

As is shown in FIGS. 15(a) and 15(b), the device which forms this eighth embodiment consists of a body fitment 80, which is fashioned out of cloth or a similar easily deformable material and to which a plurality of thermoelectric conversion elements 81 are attached. The thermoelectric conversion elements 81 are the same as those used in the device which forms the first embodiment as illustrated in FIGS. 1 and 3, and they are arranged in a checkered pattern on the body fitment 80 in such a manner that they all face in the same direction.

As is clear from FIG. 14, these thermoelectric conversion elements 81 are connected to a power supply by way of an eighth switch means 82 in such a manner that the direction of the electric current in adjacent elements is mutually similar. The eighth switch means 82 has switch elements A and B for each thermoelectric conversion element 81, and applies a forward voltage individually to the desired thermoelectric conversion elements 81, being controlled by means of the switch control unit 83. The switch control unit 83 imparts signals to the eighth switch means 82 in accordance with data showing the positions of the thermoelectric conversion elements 81 and other pre-programmed data, thus acting to open and close selectively the switch elements A and B corresponding to the thermoelectric conversion elements 81 of the eighth switch means 82.

If the body fitment 80 of the device which forms the eighth embodiment and is configured as described above is suitably deformed in such a manner that the connecting metals 84 of the thermoelectric conversion elements 81 all face inward, and if the ends of the body fitment 80 are fastened to one another by means of the fasteners 85, it is possible to hold the thermoelectric conversion elements in such a manner that the connecting metals 84 are each in close proximity to the cells which it is desired to activate, as is shown in FIG. 15(b).

Figure 16A:
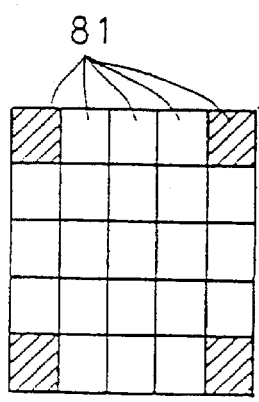
FIGS. 16(a) through 16(c) are conceptual diagrams which show the action of the device which forms a eighth embodiment as illustrated in FIG. 14.
Figure 16B:
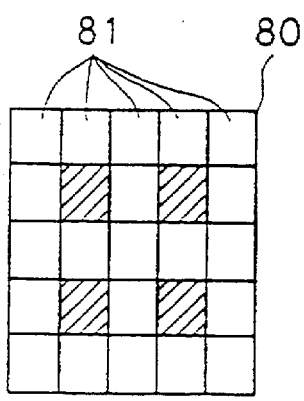
Figure 16C:
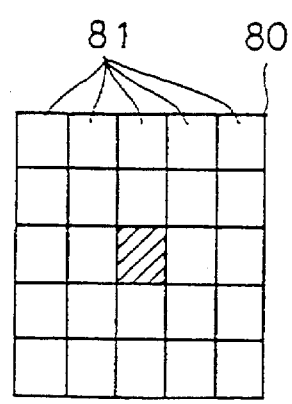

Thus, when a switch which is not shown in the drawing is turned on, forward voltage is applied in sequence to the thermoelectric conversion elements 81, for instance from the outside inward as shown in FIGS. 16(a)–16(c), in accordance with signals output from the switch control unit 83, in such a manner that high-temperature stimuli imparted from each of the thermoelectric conversion elements 83 change their position cyclically in relation to the cells, with the result that the device which forms the eighth embodiment prevents as far as possible the acclimatization to the stimuli, and allows continuous activation of cells to be achieved even during prolonged use.

The order in which voltage is applied to the thermoelectric conversion elements 81 may be changed at will by means of the data which is pre-programmed into the switch control unit 83. In this case there is no absolute need for the order to change cyclically, and it may be allowed to change at random.

FIGS. 17–19 illustrate in concept a ninth embodiment of the device for activating cells to which the present invention pertains, and show an example of a device for activating cells which achieves cell activation in the target body by imparting stimuli to that body by means of temperature.

As is shown in FIGS. 18(a) and 18(b), the device which forms the ninth embodiment consists of a band of tubes 90, which is fashioned out of resin or a similar elastic and easily deformable material. The band of tubes 90 is formed by connecting adjacent tubes 91 to one another laterally, each of the tubes 91 being connected by way of the valve unit 92 to the means of supplying hot water 93. Although they are not shown in the drawing, the valve unit 92 is equipped with electromagnetic switch-over valves for each of the tubes 91, in such a manner that it is possible to allow the desired tubes 91 to communicate individually with the abovementioned means of supplying hot water 93, this being controlled by the valve control unit 94. The valve control unit 94 imparts signals to the valve unit 92 in accordance with data showing the positions of the tubes 91 and other pre-programmed data, thus acting to operate selectively the electromagnetic switch-over valves of the valve unit 92 which correspond to each tube 91.

If the abovementioned band of tubes 90 in the device which forms the ninth embodiment and is configured as described above is suitably deformed and its ends are fastened to one another by means of fasteners which are not shown in the drawing, it is possible to hold it in such a manner that the peripheral surface of each of the tubes 91 is in close proximity to the cells which it is desired to activate, as is shown in FIG. 18(b).

Figures 19A, 19B, 19C:
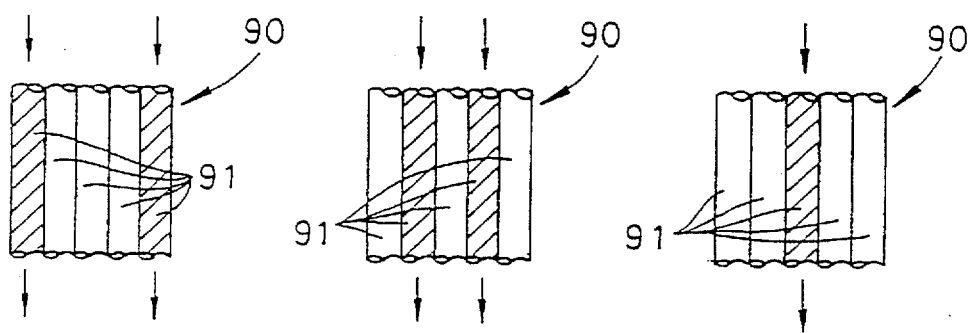
FIGS. 19(a) through 19(c) are conceptual diagrams which show the action of the device which forms the ninth embodiment as illustrated in FIG. 17.

Thus, when a switch which is not shown in the drawing is turned on, hot water is supplied in sequence to the tubes 91, for instance from the outside inward as shown in FIGS. 19(a)–19(c), in accordance with signals output from the valve control unit 94, in such a manner that high-temperature stimuli imparted from each of tubes 91 change their position cyclically in relation to the cells, with the result that the device which forms the ninth embodiment prevents as far as possible the acclimatization to the stimuli, and allows continuous activation of cells to be achieved even during prolonged use.

In the device which forms the ninth embodiment, water is supplied to the tubes 91, but it is possible to supply oil and other liquids or air and other gases instead of water. Moreover, the order in which water is supplied to the tubes 91 may be changed at will by means of the data which is pre-programmed into the valve control unit 94. In this case there is no absolute need for the order to change cyclically, and it may be allowed to change at random.

Figure 20A:
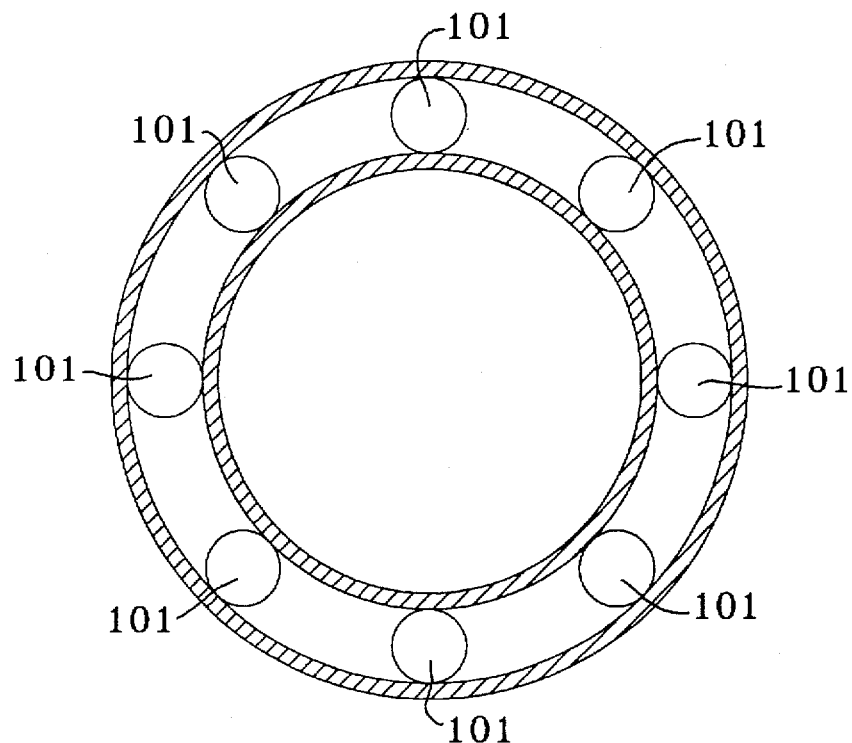
FIGS. 20(a) and 20(b) are cross-sectional diagrams which illustrate in concept a tenth embodiment of the device for activating cells to which the present invention pertains.
Figure 20B:
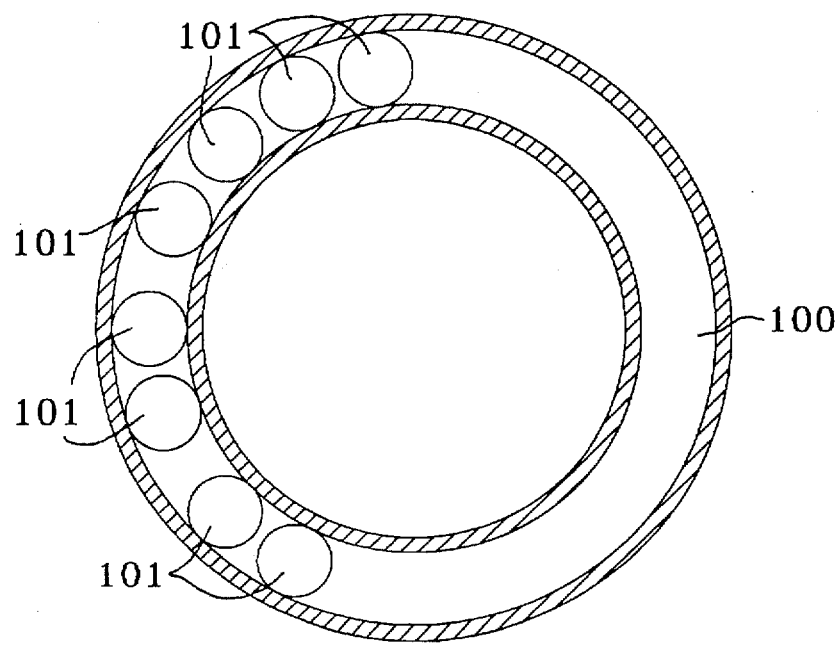

FIGS. 20(a) and 20(b) illustrate in concept a tenth embodiment of the device for activating cells to which the present invention pertains, and shows an example of a device for activating cells which achieves cell activation in the target body by imparting stimuli to that body by means of magnetism.

Figure 21:
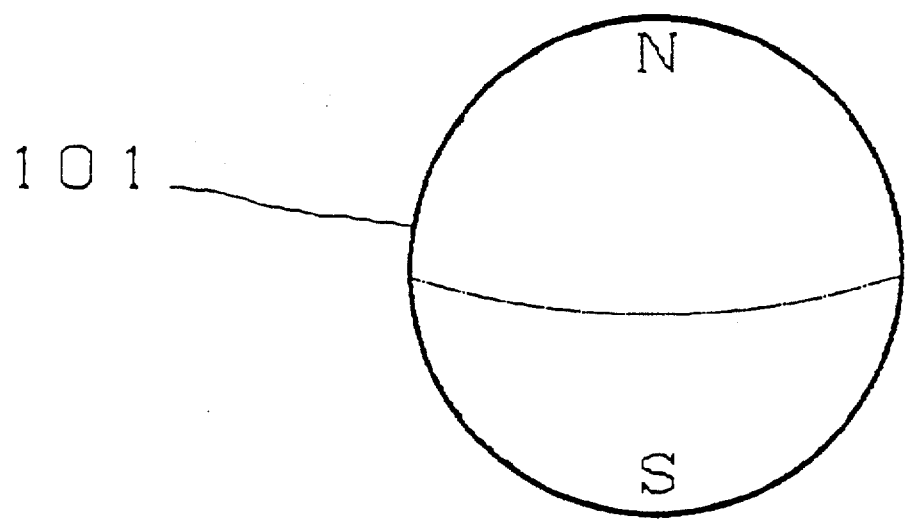
FIG. 21 is a diagonal view showing in concept the means of imparting stimuli which is employed in the device which forms the tenth embodiment as illustrated in FIG. 20.

As is shown in FIG. 20(a), the device which forms this tenth embodiment has a circular container body 100. This container body 100 is hollow and is fashioned from resin or a similar material which is elastic and easily deformable, and at the same time capable of expanding and contracting. Within this container body 100 are a plurality of permanent magnets 101. As is shown in FIG. 21, these permanent magnets 101 are fashioned spherically, all being of the same size as one another, and are arranged in such a manner that they are capable of moving by rotating within the container body 100.

Figure 22:
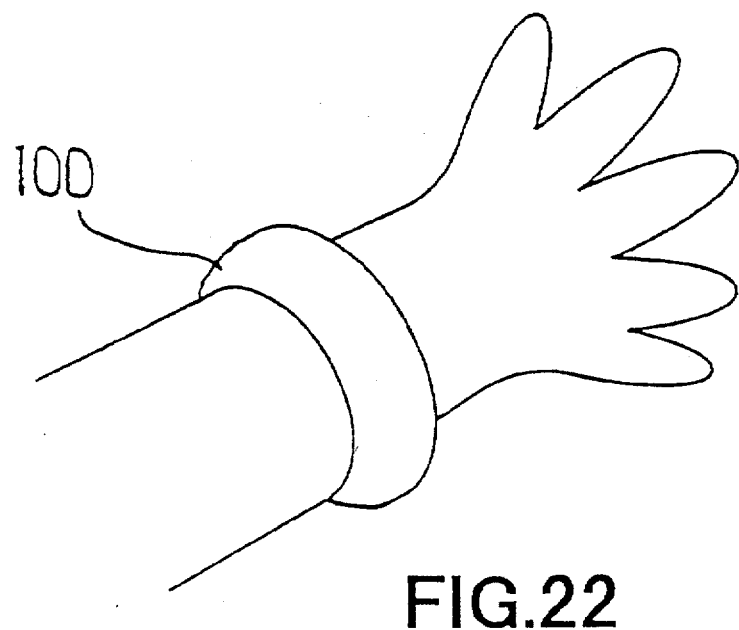
FIG. 22 is a diagonal view which shows in concept the state during use of the device which forms the tenth embodiment as illustrated in FIG. 20.

As is shown in FIG. 22, by allowing the container body 100 of the device which forms the tenth embodiment and which is configured as described above to expand and contract in a suitable manner, each of the permanent magnets 101 is held in close proximity to the cells which it is desired to activate, and stimuli are imparted by means of magnetism to such sites as are in close proximity to the permanent magnets 101.

Thus, as is shown in FIG. 20(b), when a person wearing this device walks or participates in any other form of light exercise, the permanent magnets 101 move accordingly within the container body 100 so that their respective magnetic fields and the positions in which they are located in relation to the cells change at random, with the result that the device which forms the tenth embodiment prevents as far as possible the acclimatization to the stimuli, and allows continuous activation of cells to be achieved even during prolonged use.

The device which forms the tenth embodiment employs spherical permanent magnets 101, but it is possible to achieve the same effect by employing bar-shaped permanent magnets curved to fit the container body 100.

Figure 23:
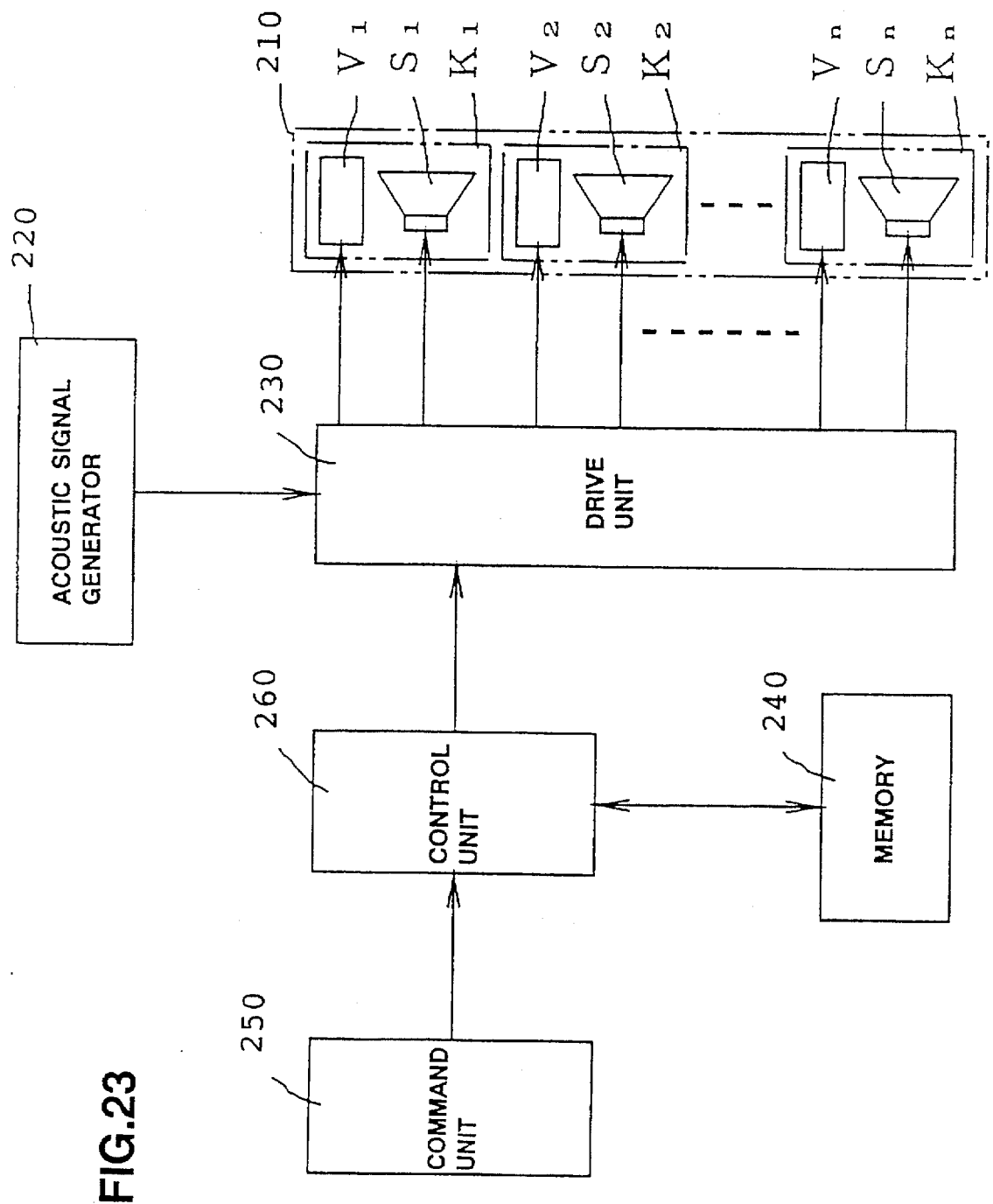
FIG. 23 is a block diagram which illustrates an eleventh embodiment of the device for activating cells to which the present invention pertains.

FIG. 23 illustrates an example of an eleventh embodiment of the device for activating cells to which the present invention pertains. In FIG. 23, the cell activation units represented by K1, K2 . . . Kn each comprises speakers or similar soundwave generators S1, S2 . . . Sn and vibrators or similar vibration generators V1, V2 . . . Vn arranged in close proximity to one another. These in turn are arranged in a prescribed pattern in several places on a mount 210.

In FIG. 23, the device for generating acoustic signals indicated by a reference numeral 220 is for instance an analogue disc player, digital disc player, tape-recorder or similar device which generates acoustic signals in the audible frequency range and can accommodate music. The acoustic signals which it generates are output to the drive unit 230.

The drive unit 230 contains a switch means not shown in the drawing for the purpose of driving selectively the cell activation units K1, K2 . . . Kn, and operates in such a manner as to impart the acoustic signals to the soundwave generator S which corresponds to the cell activation unit K of which the switch means is closed, which is to say the selected cell activation unit K, while at the same time extracting only the low-frequency range portion from the acoustic signals and imparting them to the vibration generator V of the cell activation unit K.

The memory, which is indicated in FIG. 23 by a reference numeral 240, is the unit which stores data for the purpose of driving the cell activation units K1, K2 . . . Kn in a predetermined order. It stores a plurality of data for driving these cell activation units K1, K2 . . . Kn selectively in a mutually differing order.

The command unit, which is indicated in FIG. 23 by a reference numeral 250, consists of a rotary switch, press-button switch or similar device and issues selective commands concerning the plurality of drive data stored within the memory 240, outputting the command signals corresponding to the selected drive data to the control unit 260.

The control unit 260 reads the corresponding drive data from the memory 240 in accordance with the command signals output by the command unit 250, and outputs selective drive signals to the drive unit 230 in order that it can drive the cell activation units K1, K2 . . . K5 in the order indicated by the drive data which has been read.

In the device which forms the eleventh embodiment and is configured in the abovementioned manner, selecting the desired drive data through the command unit 250 allows the cell activation units K1, K2 . . . Kn arranged on the mount 210 to be driven selectively in succession according to the order indicated by the drive data, so that soundwaves in the audible frequency range corresponding to the abovementioned acoustic signals are emitted as music from the soundwave generator S of the cell activation unit K which has been driven in this manner, and the vibration generator V in the proximity of the soundwave generator S vibrates in response to the extracted signals.

Figure 24A:
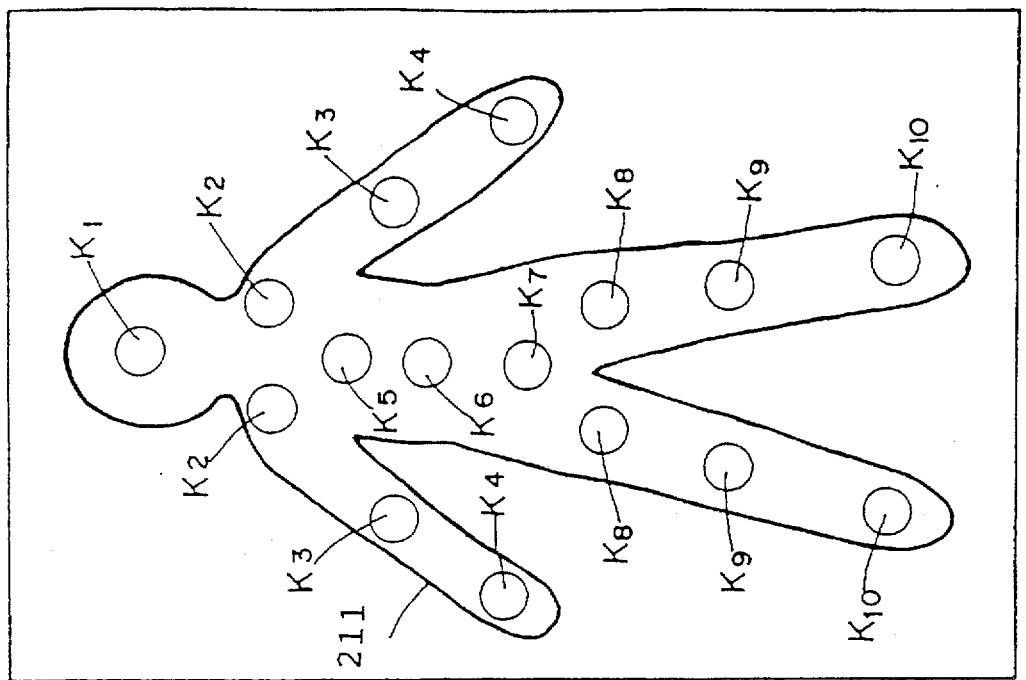
FIGS. 24(a) and 24(b) illustrate the device which forms a twelfth embodiment wherein a mount in the form of a sheet is employed in the device which forms the eleventh embodiment as illustrated in FIG. 23, FIG. 24(a) being a top view, and FIG. 24(b) a top view showing the device during use.
Figure 24B:
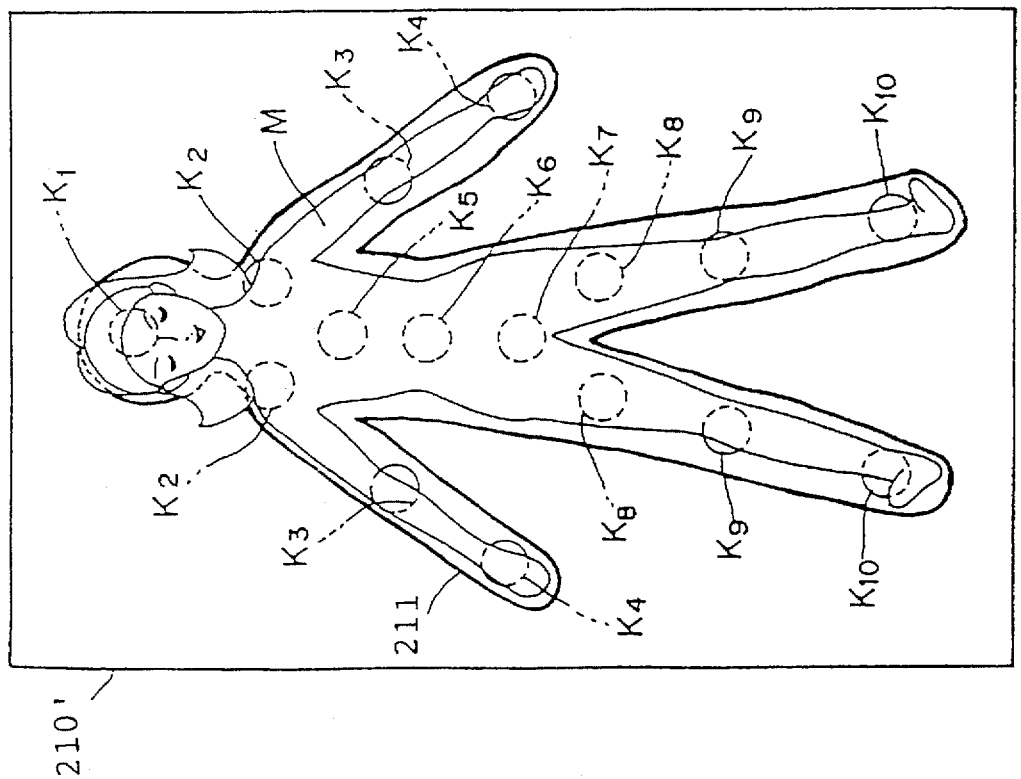

FIGS. 24(a) and 24(b) illustrate a device which forms the twelfth embodiment and which facilitates applying the device which forms the eleventh embodiment to the whole human body.

The mount 210' employed in the device which forms the twelfth embodiment uses cloth, soft resin or a similar material which deforms easily when external pressure is applied. This is fashioned into the shape of a rectangular sheet of a size such that it is able to accommodate the human body M in recumbent posture. In the center of its surface is a guideline 211, which serves to assist in positioning the human body M on the surface of the mount 210', the outline of the human body M being drawn on it in more or less actual size as is shown in FIG. 24(a).

On this mount 210' in each of several positions, to be exact 16 positions, surrounded by the guideline 211 are arranged the cell activation units K. To be more precise, within the guideline 211 are provided one head cell activation unit K1 in a position corresponding to the head of the human body M, one shoulder cell activation unit K2 each in positions corresponding to the shoulders of the human body M, one elbow cell activation unit K3 each in positions corresponding to the elbows of the human body M, one wrist cell activation unit K4 each in positions corresponding to the wrists of the human body M, one chest cell activation unit K5 in a position corresponding to the chest of the human body M, one stomach cell activation unit K6 in a position corresponding to the stomach of the human body M, one abdomen cell activation unit K7 in a position corresponding to the abdomen of the human body M, one thigh cell activation unit K8 each in positions corresponding to the thighs of the human body M, one knee cell activation unit K9 each in positions corresponding to the knees of the human body M, and one ankle cell activation unit K10 each in positions corresponding to the ankles of the human body M.

Although not shown on the drawing, each cell activation unit K is arranged in such a manner that the soundwave-generating surface of the soundwave generator S and the vibrating portion of the vibration generator V both face towards the surface of the mount 210'.

As is shown in FIG. 25, within the memory 240 of the device which forms the twelfth embodiment are a plurality of drives the purpose of which is to drive the plurality of cell activation units K1, K2 ... K10 which are arranged on the mount 210' selectively in mutually differing orders. To be more precise, A and B on the drawing are examples of drive data for the purpose of driving all the cell activation units arranged on the mount 210' selectively in a circulatory manner, while C on the drawing is an example of drive data for the purpose of driving some of the cell activation units arranged on the mount 210' selectively in a circulatory manner. Similarly, D and E on the drawing are examples of drive data for the purpose of driving all the cell activation units arranged on the mount 210' in a parallel fashion in a circulatory manner, while F and G on the drawing are examples of drive data for the purpose of driving some of the cell activation units arranged on the mount 210' selectively in a circulatory manner.

The device which forms the twelfth embodiment and is configured as described above is used by laying the mount 210' on a level surface such as a bed or floor and, as is shown in FIG. 24(b), causing the human body M to lie in a recumbent position on the surface of the mount 210' in such a manner as to fit within the guideline 211. Thus, when bodyweight is applied, the mount 210' deforms in response to the shape of the human body M, so that the device which forms the twelfth embodiment allows the vibration generators V of each cell activation unit K to come into contact without fail with the various parts of the human body.

Thus, if the command unit 250 is operated in a suitable fashion, drive data corresponding to the affected part of the human body M, for instance drive data A, is selected from among the plurality of drive data which are stored in the memory 240, and the acoustic signal generator 220 is also operated, the plurality of cell activation units K arranged on the mount 210' are driven selectively in a circulatory manner in the order K1→K2→K3→K4→K5→K6→K7→K8→K9→K10→K1, which is to say in the order shown in drive data A, soundwaves in the audible frequency range corresponding to the acoustic signals are emitted as music from the soundwave generators S of the cell activation units K driven in this manner, and the vibration generators V in the close proximity of the soundwave generators S which are emitting the music vibrate in response to the abovementioned extracted signals, thus making it possible to achieve activation of the cells which are in contact with the cell activation units K.

Thus, the location of the vibrational stimuli changes cyclically as they are imparted to the cells, with the result that the device which forms the twelfth embodiment prevents as far as possible the acclimatization to the stimuli, and allows continuous activation of cells to be achieved even during prolonged use.

Moreover, the music which is emitted from the soundwave generators S of the cell activation units K in the abovementioned device which forms the twelfth embodiment imparts stimuli in the form of aerial vibrations to the sites of the human body to which vibrations are being applied, so that it feels as if those sites are listening to the music. This allows thorough activation of the cells to be achieved because consciousness focuses naturally on those cells to which vibrations are being applied.

Furthermore, the music which is emitted from the soundwave generators S of each of the cell activation units K is perceived in an auditory manner, which has the effect of relaxing the mental state during use, thus permitting prolonged and continuous use of this device without causing any mental anguish.

Figure 26B:
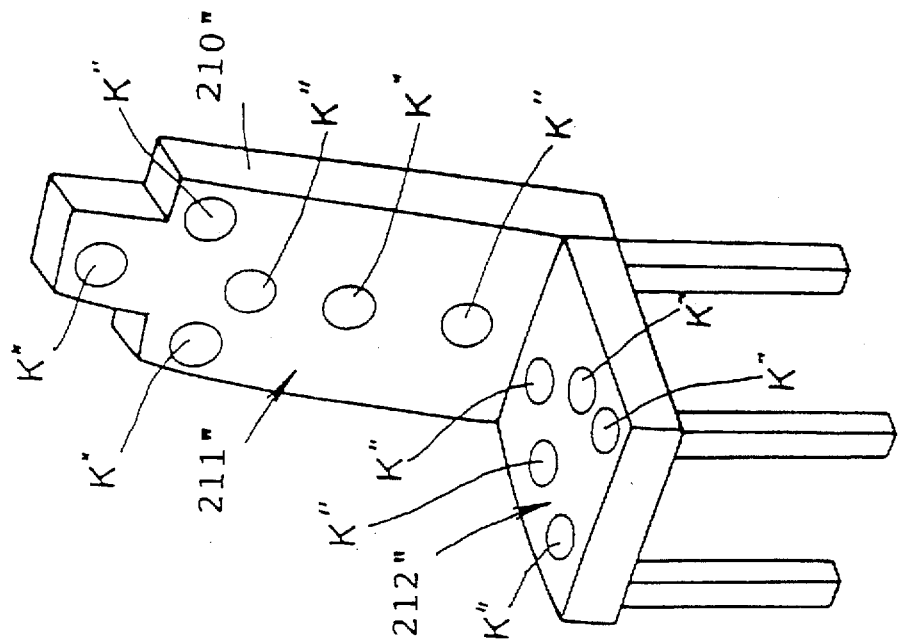
FIGS. 26(a) and 26(b) illustrate the device which forms a thirteenth embodiment wherein a mount in the form of a chair is employed in the device which forms the eleventh embodiment as illustrated in FIG. 23, FIG. 26(a) being a diagonal view, and FIG. 26(b) a diagonal view showing the device during use.
Figure 26A:
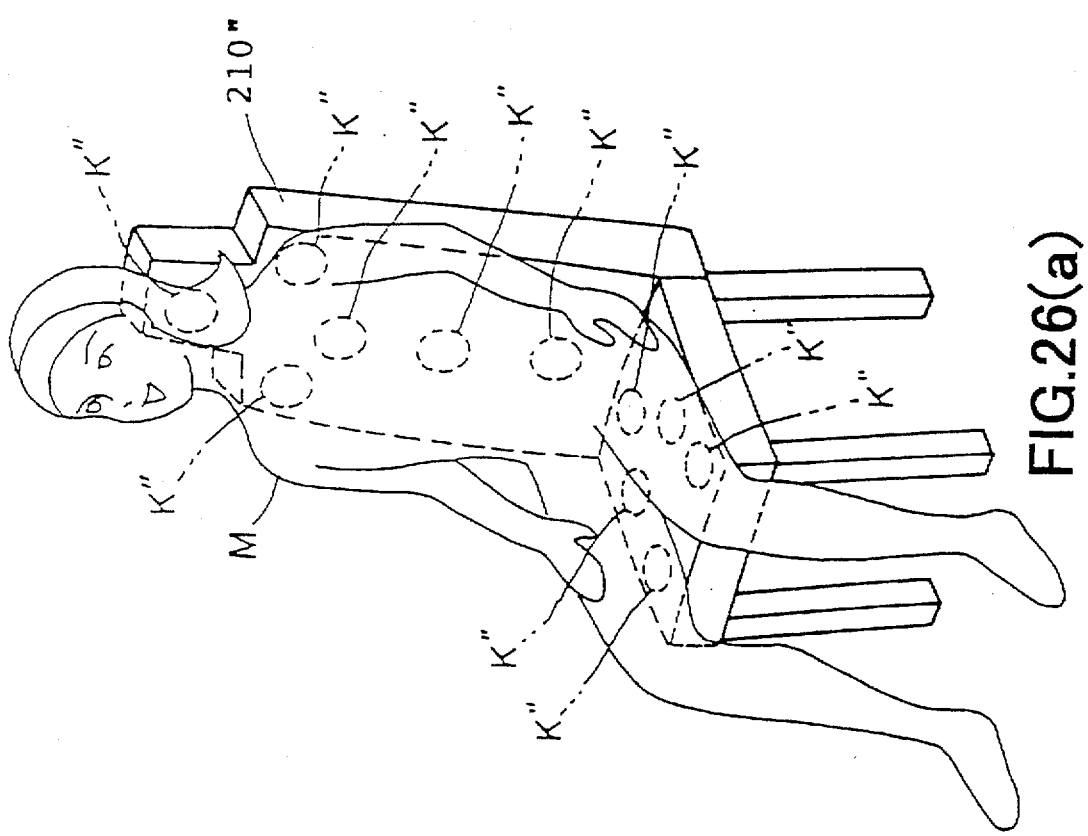

The abovementioned example of the device which forms the twelfth embodiment employs a mount in the shape of a sheet in order to impart stimuli to the whole body. However, provided that the plurality of cell activation units come into contact with a wide area of the human body, mounts of other shapes may be employed. For instance, it is possible to make use of a mount 210 in the shape of a chair on which the human body M can be sat as in the device which forms the thirteenth embodiment as illustrated in FIGS. 26(a) and 26(b). In this case, cell activation units K are located in the back-rest 211 and seat 212 respectively, thus making it possible to configure a device which activates the back and buttocks of the human body M. Moreover, in the device which forms the twelfth embodiment and employs a mount in the shape of a sheet, the mount has been laid on a bed, floor or similar horizontal surface, but the present invention is not restricted to that, and it may for instance be used by attaching it to a wall.

A–G of FIG. 25 have been adduced as examples of drive data which may be used for the purpose of driving the plurality of cell activation units in the device which forms the twelfth embodiment selectively in a predetermined order. However, there is no absolute need to drive the cell activation units this sort of order. For example, if the plurality of cell activation units are driven selectively in succession along the route of the human body, it is possible to promote the circulatory system within the human body and thus achieve further activation of cells. It is also possible to determine the duration for which each cell activation unit is driven when the plurality of cell activation units are driven selectively in a predetermined order. Furthermore, there is no absolute need to prepare several types of drive data as a single one will suffice.

In the devices which form the twelfth and thirteenth embodiments, the plurality of cell activation units are arranged to correspond with the shape of the human body. However, by arranging a number of cell activation units for instance in a checkered pattern and driving them selectively in succession, it is possible to share the device between several people of differing body shapes.

Moreover, in the device which forms the twelfth embodiment music in the audible frequency range is employed, but there is no absolute need to generate music, and it is also possible to generate soundwaves in the inaudible frequency range, which is to say supersonic and subsonic waves, alongside those in the audible frequency range. Furthermore, in the twelfth embodiment a vibration means is caused to vibrate on the basis of acoustic signals in the audible frequency range corresponding to music, but there is no absolute need to cause it to vibrate on the basis of acoustic signals corresponding to music.

Thus, the device to which the present invention pertains prevents as far as possible the acclimatization to the stimuli, the abovementioned devices which form the first to the sixth embodiments by changing the state of the stimuli which are imparted to the human body according to the desired cycle, those which form the seventh to the ninth embodiments by changing the position of the stimuli which are imparted to the human body according to the desired cycle, and those which form the tenth embodiment by changing both the state and position of the stimuli which are imparted to the human body according to the desired cycle.

In the abovementioned first to sixth embodiments, which is to say in those embodiments where the state of the stimuli is changed, the means of imparting stimuli are located in such a manner that stimuli in two adjacent places are in the opposite state to one another, but they may also be located in such a manner that stimuli in two adjacent places are the same as one another. Moreover, in the abovementioned first to sixth embodiments the state of the stimuli is changed cyclically, but the same result may also be achieved by using a random oscillator instead of a variable-frequency one, thus changing the state of the stimuli at random.

In the abovementioned seventh to ninth embodiments, which is to say in those embodiments where the position of the stimuli is changed, all the examples of means of imparting stimuli employ temperature stimuli, but it is also possible to employ means which impart magnetic or vibrational stimuli.

Figure 27:
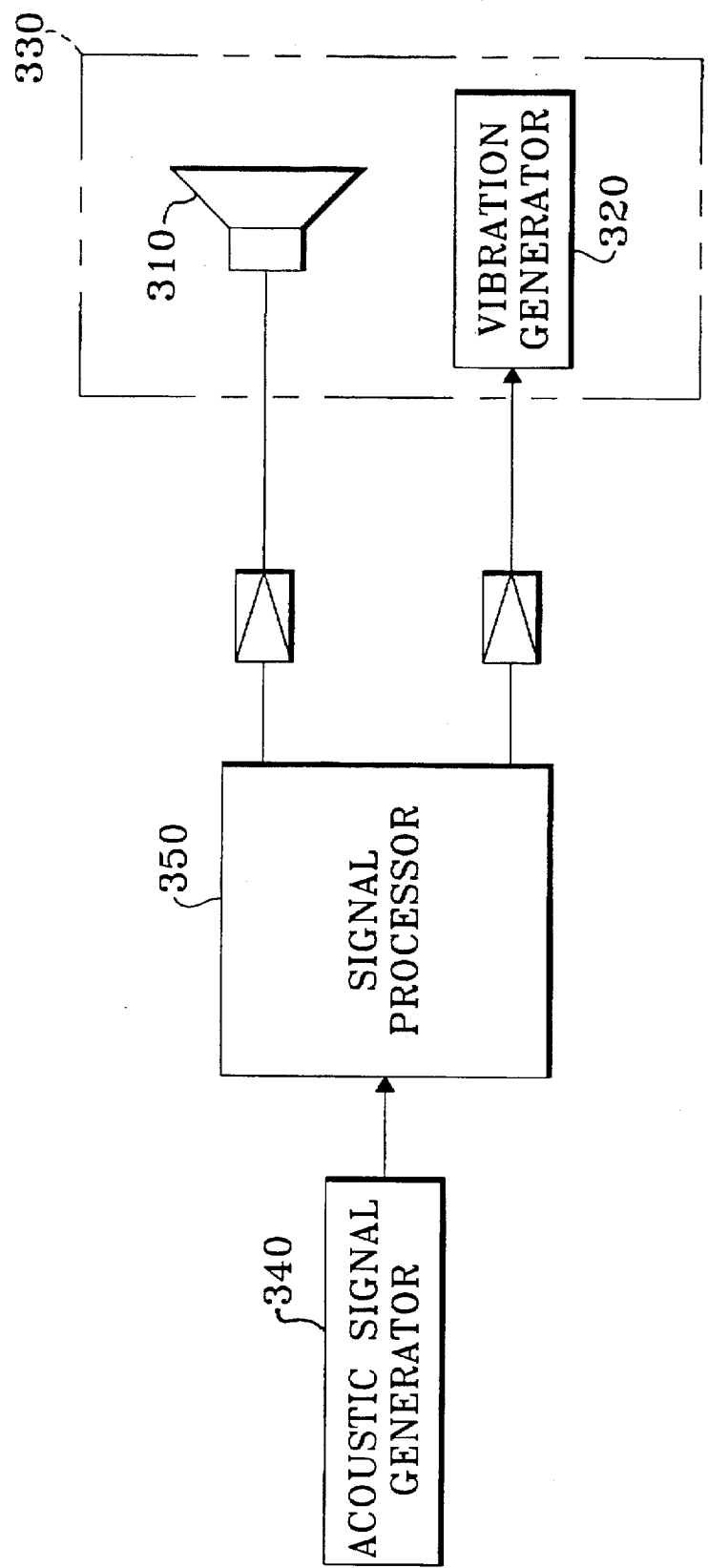
FIG. 27 is a block diagram which illustrates a fourteenth embodiment of the device for activating cells to which the present invention pertains.

FIG. 27 illustrates a device which forms the fourteenth embodiment, in which the speaker or similar soundwave generator indicated by a reference numeral 310 and the vibrator or similar vibration generator indicated by a reference numeral 320 are arranged in close proximity to one another on a body attachment 330 which may be attached to and detached from the human body.

In FIG. 27 the device for generating acoustic signals indicated by a reference numeral 340 is for instance an analogue disc player, digital disc player, tape-recorder or similar device which generates acoustic signals in the audible frequency range and can accommodate music. The acoustic signals which it generates are output to the signal processor 350.

The signal processor 350 forms signals for generating supersonic or subsonic frequencies which are modulated (by amplitude, frequency or other modulation) by the acoustic signals, mixes these signals for generating supersonic or subsonic frequencies with the acoustic signals, and imparts the mixed signals to the soundwave generator 310, while at the same time extracting only the low-frequency portion from the acoustic signals and imparting the extracted signals to the vibration generator 320.

As a result, in the body attachment 330, soundwaves corresponding to the acoustic signals are emitted as music from the soundwave generator 310, while supersonic or subsonic waves corresponding respectively to the signals for generating supersonic or subsonic waves are emitted, and the vibration generator 320 in close proximity to the soundwave generator 310 vibrates in response to the extracted signals.

Figure 28:
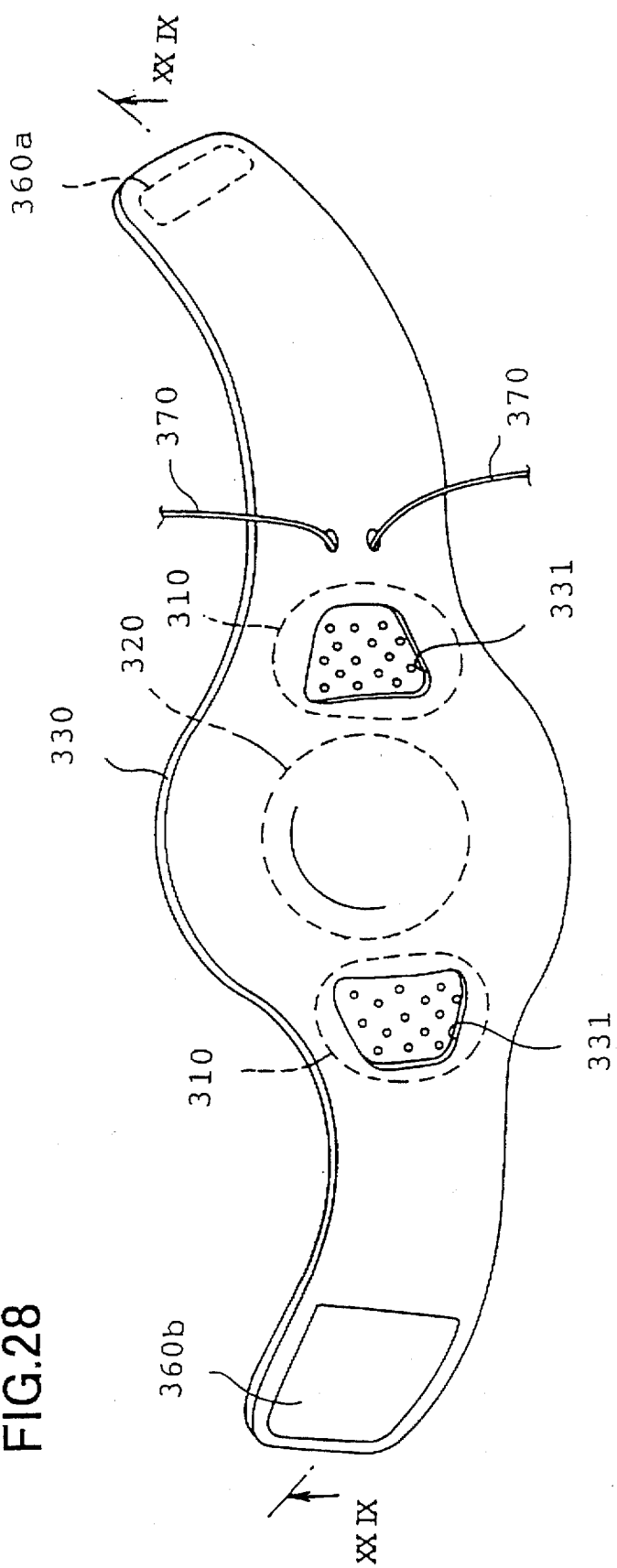
FIG. 28 illustrates in concept the device which forms a fifteenth embodiment for applying to the upper body the device which forms the fourteenth embodiment as illustrated in FIG. 27.
Figure 29:
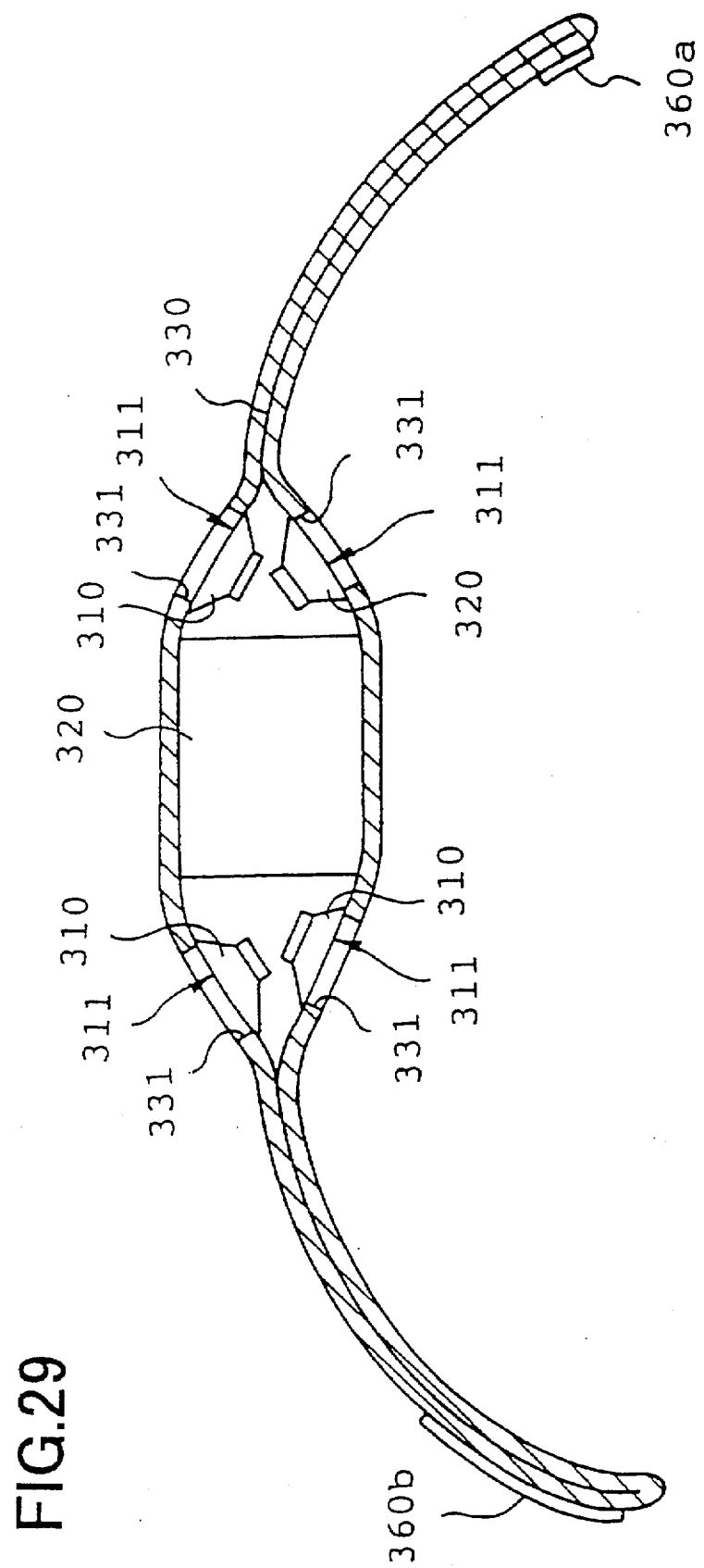
FIG. 29 is a cross-sectional diagram along line XXIX—XXIX in FIG. 28.

FIGS. 28 and 29 illustrate a fifteenth embodiment whereby the device for activating cells is applied to the stomach, back or other parts of the upper body.

The body attachment 330 which is employed in this device which forms the fifteenth embodiment uses a material which expands and contracts well, and is shaped in the form of a belt whereof the central portion protrudes in a circular shape. Inside in the center of this protruding portion is fitted the vibration generator 320, while on either side of this vibration generator 320 are located two of the soundwave generators 310. Either end of the belt is provided with fasteners 360a and 360b which are capable of interlocking.

As is clear from FIG. 29, the vibration generator 320 is attached at both ends front and rear to the inner surface of the body attachment 330 so that the vibrations when it is driven are easily propagated in an outward direction. The soundwave generators 310 are fitted to the body attachment 330 in such a manner that the surfaces from which soundwaves are emitted from a soundwave emitting surface 311 towards perforations 331 formed in the front and rear surfaces of the body attachment 330.

A reference numeral 370 in FIG. 28 denotes leads for transmitting the mixed signals and extracted signals output from the signal processor 350 to the vibration generator 320 and soundwave generators 310 respectively.

Figure 30:
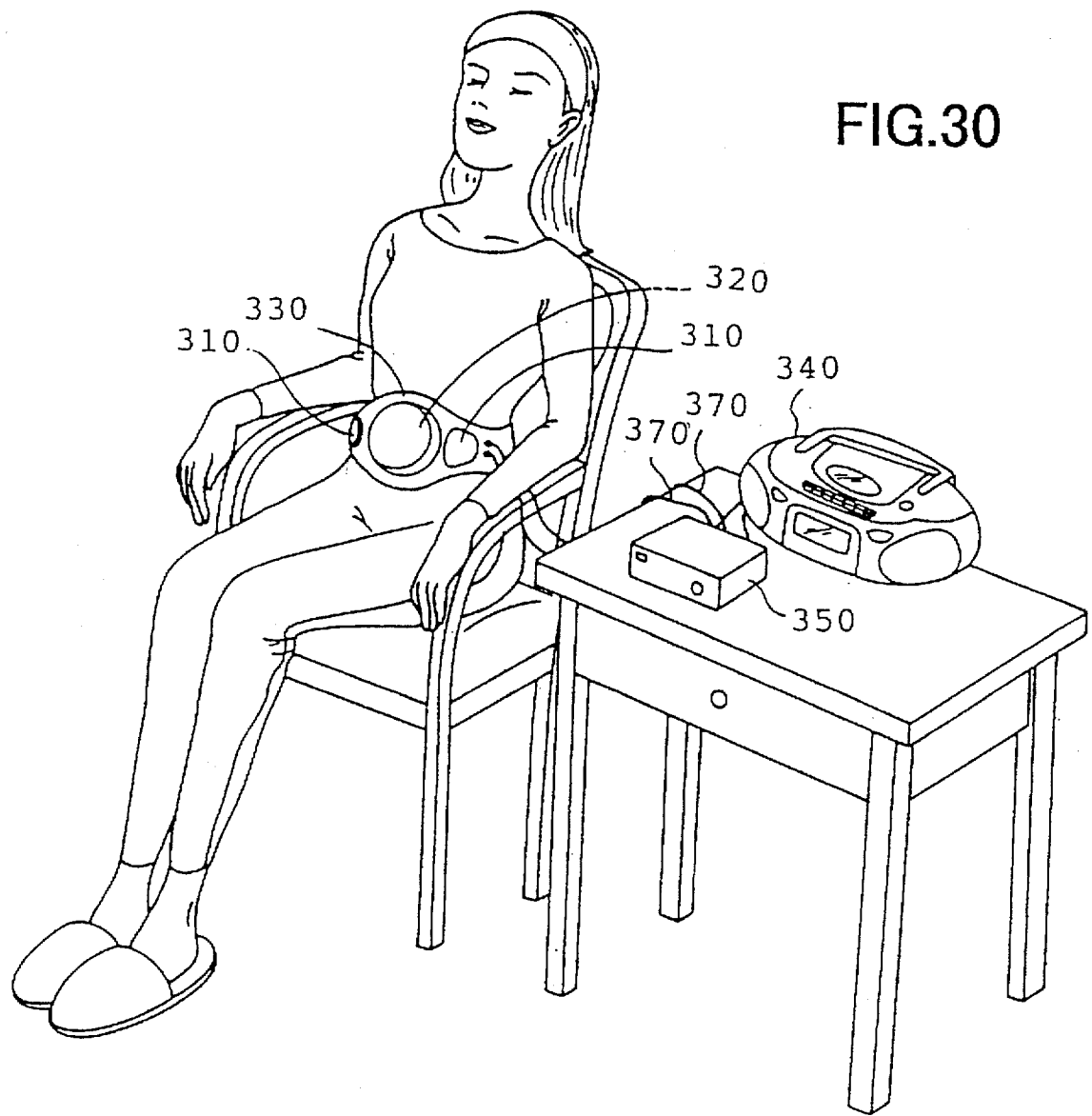
FIG. 30 is a conceptual diagram which illustrates the state during use of the device which forms the fifteenth embodiment as illustrated in FIG. 29.

The device which forms the fifteenth embodiment and is configured as described above is worn by fastening the fasteners 360a and 360b which are provided at either end of the body attachment 330 together in a suitable position in such a manner that the portion which houses the vibration generator 320 is in close contact with part of the upper body, the stomach for example as shown in FIG. 30.

Thus, when the acoustic signal generator 340 is operated, vibrational stimuli are imparted directly to the stomach as a result of the vibrations of the vibration generator 320 in response to the extracted signals, thus activating the cells of the stomach by means of the vibrations.

Because soundwaves corresponding to the acoustic signals are emitted as music from the soundwave generators 310, it is possible to relax the mental state through the auditory sense, thus permitting prolonged and continuous use of the device which forms the fifteenth embodiment without causing any mental anguish.

Moreover, if mixed supersonic wave generating signals and acoustic signals are imparted to the soundwave generator 310 from the signal processor 350, supersonic waves corresponding to the supersonic wave generating signals, which is to say supersonic waves related to the music are emitted from the soundwave generator 310 along with the music, and these supersonic waves are imparted in the form of stimuli resulting from aerial vibrations deep into the stomach, so that it feels as if the cells of the stomach are listening to the music. This allows thorough activation of the cells of the stomach to be achieved because consciousness focuses naturally on those cells.

On the other hand, if mixed subsonic wave generating signals and acoustic signals are imparted to the soundwave generator 310 from the signal processor 350, subsonic waves corresponding to the subsonic wave generating signals, which is to say subsonic waves related to the music are emitted from the soundwave generator 310 along with the music, and these subsonic waves are imparted in the form of stimuli resulting from aerial vibrations deep into the stomach, so that it feels as if the cells of the stomach are listening to the music. This allows thorough activation of the cells of the stomach to be achieved because consciousness focuses naturally on those cells.

Figure 31:
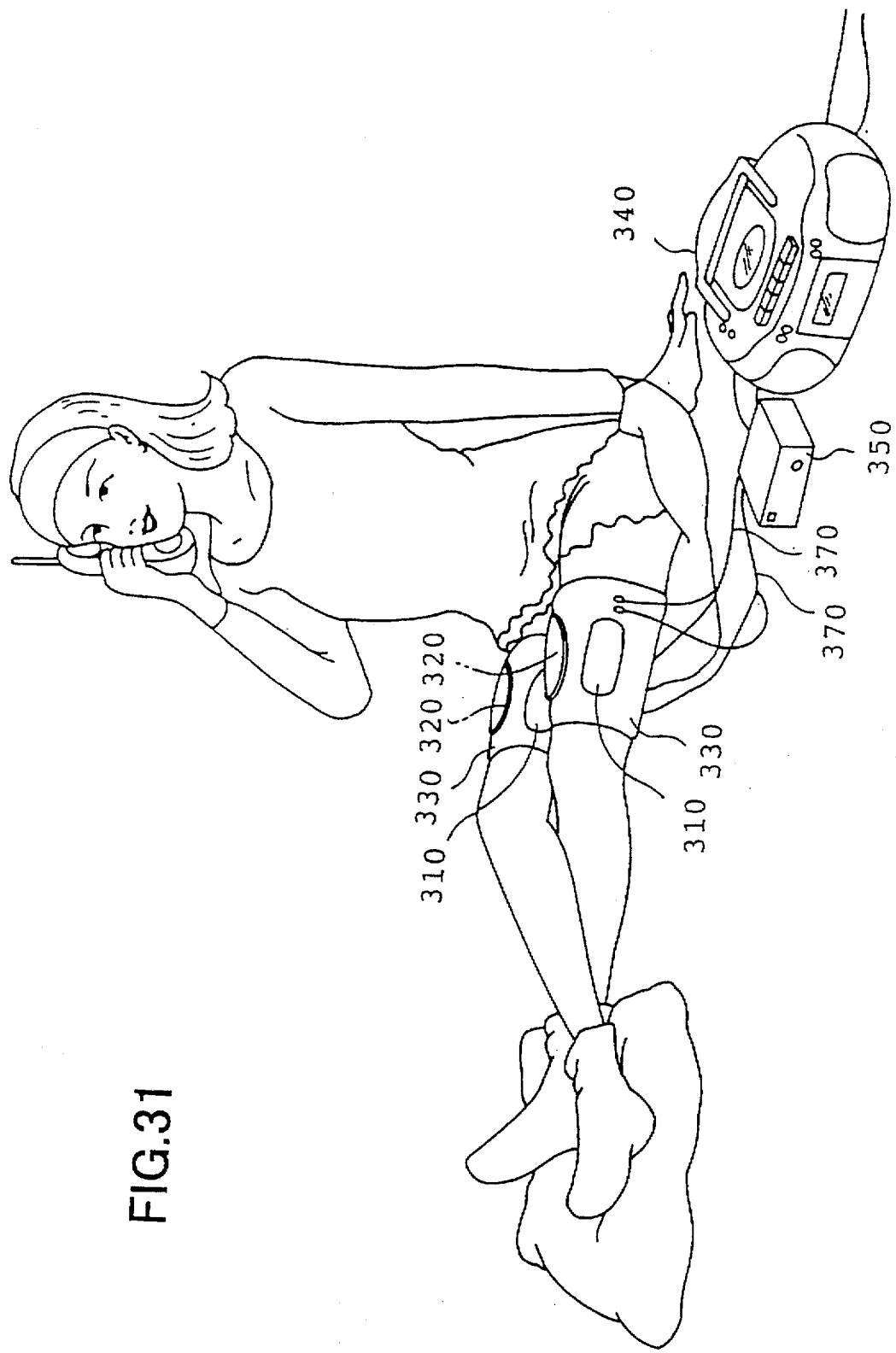
FIG. 31 is a conceptual diagram which illustrates the device which forms the fourteenth embodiment as illustrated in FIG. 27 in use on the thigh.
Figure 32:
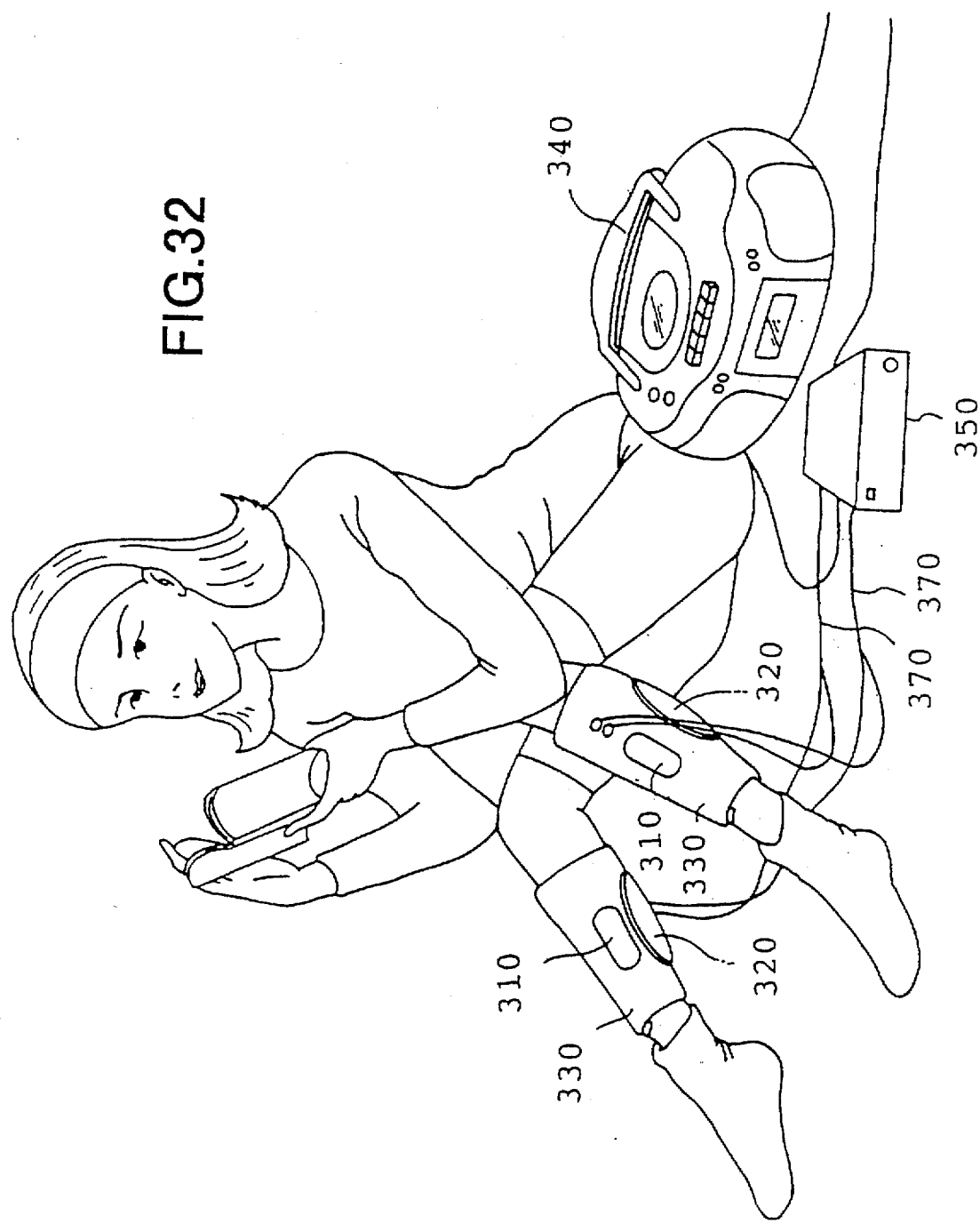
FIG. 32 is a conceptual diagram which illustrates the device which forms the fourteenth embodiment as illustrated in FIG. 27 in use on the crus.

In the abovementioned devices which form the fourteen and fifteenth embodiments, the means for imparting vibrational stimuli and soundwaves are held against the human body in a body attachment which can be attached and detached. However, there is no absolute need in the present invention to hold the means for imparting vibrational stimuli and soundwaves against the human body in a body attachment which can be attached and detached, and they can be contained for instance in a foot-rest. It should be added that examples have been shown where the fifteenth embodiment is applied to the stomach, back or other parts of the upper body, but by changing the shape of the body attachment in a suitable fashion, to fit the thigh for instance as in FIG. 31 or the abdomen as in FIG. 32, the device can be configured for use on other affected parts as desired.

Moreover, in the devices which form the fourteenth and fifteenth embodiments, soundwaves in both the audible and inaudible frequency ranges have been generated simultaneously from the means for imparting soundwaves, but it is sufficient to generate soundwaves in either one of the frequency ranges. Furthermore, where soundwaves in both frequency range are generated, the same soundwave generator has been used in the devices which form the fourteenth and fifteenth embodiments, but it is also possible to configure them in such a manner that soundwaves in the audible and inaudible frequency ranges are generated from separate soundwave generators provided for each of them.

Additionally, in the devices which form the fourteenth and fifteenth embodiments, soundwaves corresponding to music have been generated from the means for generating soundwaves for the affected parts, but there is no absolute need to generate soundwaves corresponding to music.

What is claimed is:

1. A device for activating the cells of a human body, comprising:

a body attachment adapted to be removably attached to the human body;

vibration stimuli imparting means mounted on said body attachment, said vibrations stimuli means imparting vibration stimuli to the human body in response to a drive signal supplied thereto;

soundwave generating means mounted on said body attachment, for generating soundwaves to the human body in a vicinity of said vibration stimuli imparting means in response to a drive signal supplied thereto; and signal processor means for forming a signal for generating a supersonic wave and/or a signal for generating a subsonic wave, said signals being modulated by an acoustic signal supplied from an external source, mixing said signal for generating said supersonic wave and/or said signal for generating said subsonic wave with said acoustic signal to form a mixed drive signal, supplying said mixed drive signal to said soundwave generating means, and extracting a low-frequency portion from said acoustic signal to form an extracted drive signal and supplying said extracted drive signal to said vibration stimuli imparting means.

* * * * *